(12) United States Patent
Saito et al.

(10) Patent No.: US 12,091,775 B2
(45) Date of Patent: Sep. 17, 2024

(54) RNA STRUCTURE LIBRARY

(71) Applicant: KYOTO UNIVERSITY, Kyoto (JP)

(72) Inventors: Hirohide Saito, Kyoto (JP); Kaoru Richard Komatsu, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 1635 days.

(21) Appl. No.: 16/313,329

(22) PCT Filed: Jun. 27, 2017

(86) PCT No.: PCT/JP2017/023607
§ 371 (c)(1),
(2) Date: Feb. 28, 2019

(87) PCT Pub. No.: WO2018/003809
PCT Pub. Date: Jan. 4, 2018

(65) Prior Publication Data
US 2022/0307159 A1 Sep. 29, 2022

(30) Foreign Application Priority Data
Jun. 27, 2016 (JP) .................................. 2016-127002

(51) Int. Cl.
| | | |
|---|---|---|
| C40B 40/06 | (2006.01) | |
| C12N 15/09 | (2006.01) | |
| C12Q 1/6811 | (2018.01) | |
| C12Q 1/6876 | (2018.01) | |
| C40B 20/04 | (2006.01) | |

(52) U.S. Cl.
CPC .............. *C40B 40/06* (2013.01); *C12N 15/09* (2013.01); *C12Q 1/6811* (2013.01); *C12Q 1/6876* (2013.01); *C40B 20/04* (2013.01)

(58) Field of Classification Search
None
See application file for complete search history.

(56) References Cited

U.S. PATENT DOCUMENTS

| 2009/0019042 A1 | 1/2009 | Nakamura et al. |
| 2015/0292005 A1 | 10/2015 | Tomita et al. |
| 2017/0022545 A1* | 1/2017 | Saito et al. .......... C12Q 1/6811 |

FOREIGN PATENT DOCUMENTS

| JP | 2002191368 | 7/2002 | |
| JP | 2007226700 | 9/2007 | |
| WO | 2006/054788 | 5/2006 | |
| WO | 2013/161964 | 10/2013 | |
| WO | 2015/105179 | 7/2015 | |
| WO | WO-2015105179 A1 * | 7/2015 | .......... C12Q 1/6806 |

OTHER PUBLICATIONS

Hamada et al. "Mining frequent stem patterns from unaligned RNA sequences", Bioinformatics 22(20):2480-2487 (2006).
Hamada et al. "Predication of RNA secondary structure using generalized centroid estimators", Bioinformatics 25 (4):465-473 (2009).
Saito et al. "RNA functional/structural motifs that lurk in genome", Cell Technology 28(2):143-148 (2009).
Komatsu et al. "The screening system of RNA motif binding to arbitrary proteins by using Microarray", 17th RNA meeting in Sapporo (2015) 3 pages.
Keene "RNA regulons: coordination of post-transcriptional events", Nature Reviews Genetics 8:533-543 (2007).
Lambert et al. "RNA Bind-n-Seq: Quantitative Assessment of the Sequence and Structural Binding Specificity of RNA Binding Proteins", Molecular Cell 54:887-900 (2014).
Ray et al. "Rapid and systematic analysis of the RNA recognition specificities of RNA-binding proteins", Nature Technology 27(7):667-670 (2009).
Ray et al. "A compendium of RNA-binding motifs for decoding gene regulation", Nature 499:172-177 (2013).
Weingarten-Gabbay et al. "Systematic discovery of cap-independent translation sequences in human and viral genomes", Science 351(6270):aad4939-1-aad4939-13 (2016).
International Search Report corresponding to International Application No. PCT/JP2017/023607 mailed Sep. 26, 2017.

* cited by examiner

*Primary Examiner* — Kaijiang Zhang
(74) *Attorney, Agent, or Firm* — Myers Bigel, P.A.

(57) ABSTRACT

An RNA probe containing RNA functional structural units is prepared by the following steps: (1) recognizing one or more stem structures contained in the RNA based on RNA sequence information; (2) extracting a motif region with reference to the one or more recognized stem structures; (3) adding an assistive stem region to the extracted motif region; and (4) adding a barcode region, which represents a complementary sequence to a DNA barcode sequence, to the assistive stem region. Also provided is a method for detecting a protein-binding RNA by using an RNA probe containing RNA functional structural units.

1 Claim, 41 Drawing Sheets
Specification includes a Sequence Listing.

STRUCTURAL INFORMATION OF Pre-miRNA RECORDED ON miRBase

RELATIVE PREFERENCE

RANK15
pre-hsa-let-7d

RANK5
pre-hsa-mir-98

RANK2
5' UTR OF GYG1

—— GNGAY(Y=C or U)
▓▓▓ SEQUENCE RICH IN AG

ANTI-EIF3A

ANTI-EIF3B

ANTI-EIF3D

RANK1

RANK2

RANK3

RANK5

RANK6

RANK7

RANK8

RANK9

RANK10

RANK11

RANK12

RANK13

RANK14

RANK15

RANK16

RANK8615

RANK8616

RANK8617

RANK8618

RANK8619

RANK8620

RANK8621

RANK8622

RANK8623

RANK8625

RANK8626

RANK8627

RANK8628

RANK8629

RANK8630

RANK19
>HIV_2014_SIEGFRIED_NUCS_1_753_9
(HIV-1 GAG IRES)

RNA STRUCTURE LIBRARY

RELATED APPLICATIONS

This application is a 35 U.S.C. § 371 national phase application of PCT Application PCT/JP2017/023607 filed Jun. 27, 2017, which claims priority to Japanese Application No. 2016-127002 filed Jun. 27, 2016. The entire contents of each are incorporated herein by reference in its entirety.

FIELD OF THE INVENTION

The present invention relates to an RNA library based on RNA secondary structural units and to a screening method using the same.

BACKGROUND OF THE INVENTION

In recent years, RNAs, which themselves act as functional molecules without being translated into proteins, so-called noncoding RNAs or functional RNAs, have attracted attention. For example, it has been known that functional RNAs specifically interact with proteins to form RNA-protein (RNP) complexes and regulate molecular mechanisms such as gene expression and splicing (Non-Patent Document 1). For the functional RNAs, their conformations are thought to be important for their functions similar to those of proteins, and the RNP interactions are greatly influenced by the structural changes of the RNAs. Therefore, it has also reported that the failure in functions of the RNAs caused by structural abnormalities of the RNAs is involved in the risk for onset of diseases. In addition, for example, internal ribosome entry sites (IRESs) have been known as protein expression regulatory sequences present in noncoding regions of mRNAs, but the functions of IRESs are also regulated by their conformations and greatly influenced by the changes in the conformations. Thus, the noncoding RNAs having specific structures plays various roles important for functions of life, and functional analyses of RNAs focusing on the structures of RNAs are surely essential in medical and biological research.

In recent years, analyses of RNP interactions using RNA libraries, based on the RNA Bind-n-Seq method (Non-Patent Document 2) and the RNAcompete method (Non-Patent Documents 3 and 4) and the like, have been performed. However, in these methods, short artificially-synthesized RNA sequences randomly generated have been to be analyzed, and there has been a problem in that they cannot analyze complicated high-order RNA structures existing in vivo. Studies for identifying IRESs contained in human and viral genome sequences have also been performed (Non-Patent Document 5), but in this study, RNAs to be analyzed have been segmented into short random sequences because the lengths of RNAs contained in the library are limited. Therefore, many non-existing RNA structures are contained in the library, while the original RNA structures are not conserved, which results in many false-negatives and false positives, and thus, causes problems that RNA functional structures cannot be accurately analyzed.

Accordingly, the present inventors have established a method for analyzing RNP interaction using an RNA library based on structural information of pre-miRNAs registered in the miRBase, as a method for analyzing a functional RNA reflecting the structure of an RNA existing in vivo (Patent Document 1). However, in this method, RNA structures other than the loop structures of the miRNA precursors registered in the miRBase cannot be included in the library, so that there has been a problem that the analysis can be performed only on very limited RNA structures and the versatility is thus low.

CITATION LIST

Patent Document

Patent Document 1: WO 2015/105179
Non Patent Documents
Non-Patent Document 1: Keene, J. D., Nat. Rev. Genet., Vol. 8, pp. 533-543 (2007)
Non-Patent Document 2: Lambert, N. et al., Mol. Cell, Vol. 54, pp. 887-900 (2014)
Non-Patent Document 3: Ray, D. et al., Nat. Biotechnol., Vol. 27, pp. 667-670 (2009)
Non-Patent Document 4: Ray, D. et al., Nature, Vol. 499, pp. 172-177 (2013)
Non-Patent Document 5: Weingarten-Gabbay, S. et al., Science, Vol. 351, aad4939-aad4939 (2016)

SUMMARY OF INVENTION

Technical Problem

The object of the present invention is to solve the problems of the prior arts and to provide an RNA library comprising functional structural units extracted from a wide variety of RNAs.

Solution to Problem

The present inventors have intensively researched and, as a result, have succeeded in accurately extracting RNA functional structural units based only on RNA sequence information, and thus producing an RNA library by which structures of RNAs existing in vivo are reproduced.

Accordingly, the present invention provides the following:

[1] A method for preparing an RNA probe, comprising the following steps:
 (1) recognizing one or more stem structures contained in an RNA based on RNA sequence information;
 (2) extracting a motif region with reference to the one or more recognized stem structures;
 (3) adding a first assistive stem portion sequence and a second assistive stem portion sequence to the extracted motif region, wherein the second assistive stem portion sequence is complementary to the first assistive stem portion sequence and hybridizes to the first assistive stem portion sequence to form a double-stranded assistive stem; and
 (4) adding a barcode region, which represents a complementary sequence to a DNA barcode sequence, to the assistive stem region.

[2] The method according to [1], wherein the step (2) comprises:
 (2a) selecting one or more stem structures from the recognized stem structures;
 (2b) replacing the selected stem structures by a putative loop structure; and
 (2c) changing the stem structures to be selected and repeating the steps (2a) and (2b).

[3] An RNA probe comprising the following regions (1) to (3):
  (1) a barcode region which represents a complementary sequence to a DNA barcode sequence;
  (2) an assistive stem region comprising a first assistive stem portion sequence and a second assistive stem portion sequence, wherein the second assistive stem portion sequence is a sequence complementary to the first assistive stem portion sequence and hybridizes to the first assistive stem portion sequence to form a double-stranded assistive stem; and
  (3) a motif region which links the first assistive stem portion with the second assistive stem portion, the motif region comprising a sequence forming a higher-order structure having a multi-branched loop portion.

[4] The RNA probe according to [3], wherein the complementary sequence to the DNA barcode sequence is a sequence which forms no base pair or pseudo-knot with the assistive stem region and/or the motif region.

[5] The RNA probe according to [3] or [4], wherein the 5' end of the complementary sequence to the DNA barcode sequence is a base other than uracil.

[6] The RNA probe according to any one of [3] to [5], which is fluorescently labeled at its 3' end.

[7] An RNA probe library comprising a plurality of the RNA probes according to any one of [3] to [6], wherein the RNA probes each contain a motif region having a different sequence.

[8] A kit for RNA analysis comprising a microarray having DNA barcode sequences immobilized on a support, and the RNA probe library according to [7].

[9] An RNA microarray prepared by hybridizing a microarray having DNA barcode sequences immobilized on a support with the RNA probe library according to [7].

[10] A method for detecting an RNA which binds to a protein, comprising the following steps:
  (1) contacting the RNA probe according to any one of claims [3] to [6] with a target protein;
  (2) isolating a conjugate of the RNA probe obtained in the step (1) and the target protein;
  (3) extracting the RNA probe from the conjugate isolated in the step (2),
  (4) contacting the RNA probe extracted in the step (3) with a microarray having DNA barcode sequences immobilized on a support;
  (5) identifying the RNA probe hybridized with one of the DNA barcode sequences in the step (4); and
  (6) detecting an RNA containing a sequence of a motif region of the RNA probe identified in the step (5) as the RNA which binds to the target protein.

Advantageous Effects of Invention

According to the present invention, the RNA functional structural units are included in the RNA library without being segmented, and it therefore becomes possible to analyze the functions of large RNA structural units containing a plurality of loop structures, which have been heretofore difficult to analyze. In addition, since the RNA functional structural units can be extracted based only on RNA sequence information, it is possible to analyze the functional structural units extracted from a wide variety of RNAs.

DESCRIPTION OF EMBODIMENTS

The present invention will be described in detail below but will not be limited to the embodiments described herein.

The present invention provides a method for preparing an RNA probe, comprising the following steps:
  (1) recognizing one or more stem structures contained in an RNA based on RNA sequence information;
  (2) extracting a motif region with reference to the one or more recognized stem structures;
  (3) adding a first assistive stem portion sequence and a second assistive stem portion sequence to the extracted motif region, wherein the second assistive stem portion sequence is complementary to the first assistive stem portion sequence and hybridizes to the first assistive stem portion sequence to form a double-stranded assistive stem; and
  (4) adding a barcode region, which represents a complementary sequence to a DNA barcode sequence, to the assistive stem.

Figure 1A:
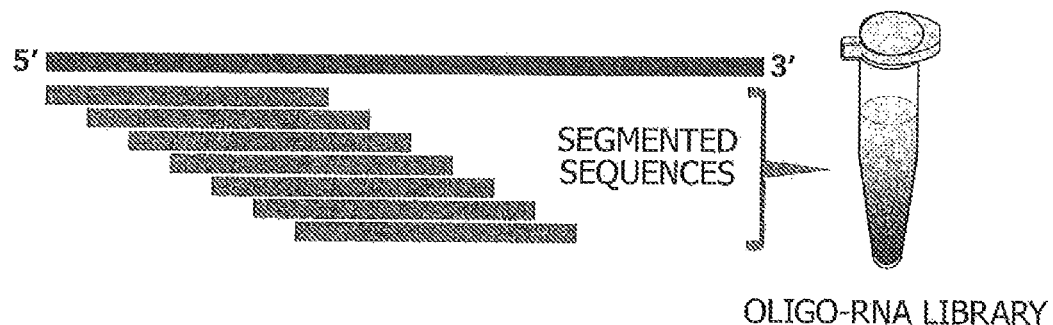
FIG. 1 is a diagram showing the outline of a method for preparing an RNA library that is conventionally known.
Figure 1B:
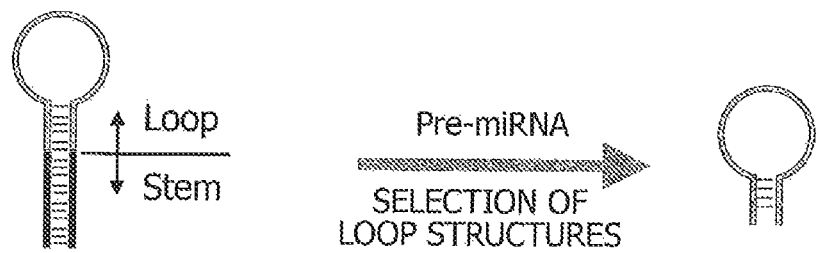
Figure 2A:
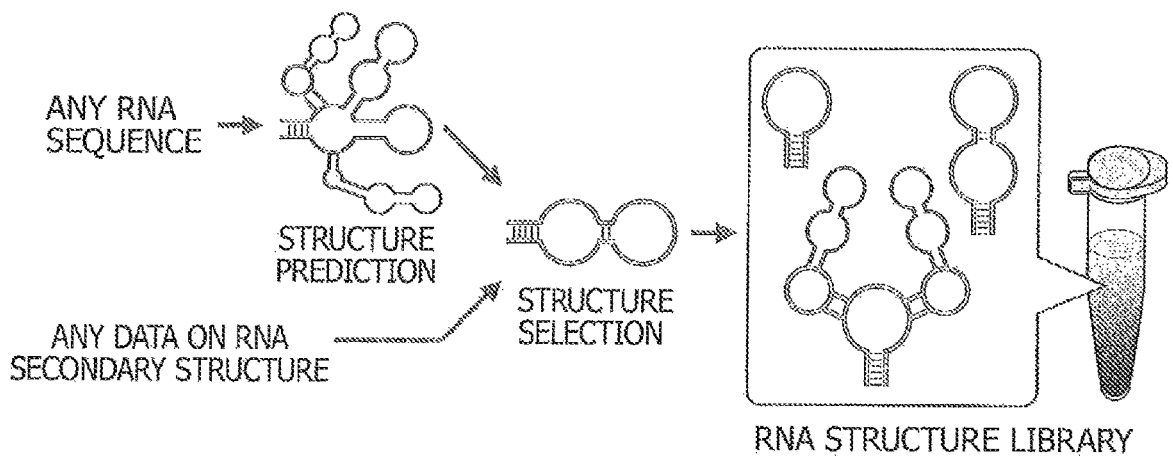
FIG. 2 is a diagram showing the outline of a method for preparing an RNA library according to the present invention.

The outline of a method for preparing an RNA library that is conventionally known is shown in FIG. 1, and the outline of a method for preparing an RNA probe according to the present invention is shown in FIG. 2a. As shown in FIG. 2a, the method for preparing an RNA probe according to the present invention is to prepare an RNA probe based on a functional structural unit of an RNA by extracting a motif region which is the RNA functional structural unit from any RNA sequence information.

The RNA probe of the present invention refers to a nucleic acid molecule containing an RNA having a sequence that may interact with a target substance, preferably a nucleic acid molecule comprising an RNA. In the present invention, the target substance is preferably a protein.

In the method for preparing an RNA probe according to the present invention, one or more stem structures contained in an RNA are recognized based on RNA sequence information.

In the present invention, the term "stem structure" refers to a double helical structure formed by any nucleic acid sequence contained in an RNA and a sequence complementary to the nucleic acid sequence. In the present invention, the term "complementary" means that two nucleic acid sequences can hybridize with each other. The two nucleic acid sequences constituting the stem structure may be complementary at least 70%, 75%, 80%, 85%, 90%, 95%, 99% or 100% in sequence to each other, because the two sequences may hybridize with each other.

In the method for preparing an RNA probe according to the present invention, the stem structure in the RNA can be recognized, for example, by using an RNA secondary structure prediction software such as CentroidFold (Hamada, M. et al., Bioinformatics, Vol. 25, pp 465-473, 2009) or IPknot (Sato, K. et al., Methods Biochem. Anal., Vol. 27, pp. i85-i93, 2011).

In the method for preparing an RNA probe according to the present invention, it is possible to use any RNA sequence information, for example, one downloaded from an RNA sequence data base such as UTRdb (Grillo, G. et al., Nucl. Acids Res., Vol. 38, D75-D80, 2010), IRESite (Mokrejs, M. et al., Nucl. Acids Res., Vol. 38, D131-D136, 2010), GenBank (Benson, D. et al., Nucl. Acids Res., Vol. 41, D36-D42, 2013) or RNAcentral (RNAcentral Consortium, Nucl. Acids Res., Vol. 43, D123-D129, 2015). RNA sequence information may be also obtained from databases containing not only RNA sequence information but also RNA structure information. For example, the RNA sequence information downloaded from Rfam (Nawrocki, E. P. et al., Nucl. Acids Res., Vol. 43, D130-D137, 2015), Structure Surfer (Berkowitz, N. D. et al., BMC Bioinformatics, Vol. 17, p. 215, 2016) or the like can be used.

Then, a motif region in the RNA is extracted with reference to the recognized stem structure(s) in the RNA.

In the present invention, the term "motif region" refers to a functional structural unit for an RNA to interact with a target substance. The motif region extracted in the method for preparing an RNA probe according to the present invention may have a single stem-loop structure (hairpin loop structure) or a plurality of stem-loop structures (multi-branched loop structure). According to the method for preparing an RNA probe according to the present invention, it is possible to prepare the RNA probe reflecting the functional structural unit existing in the RNA without segmenting the motif region because the motif region is extracted with reference to the stem structure. The motif region may have any sequence length so long as its function is maintained, and may have, for example, 500 bases or fewer, 400 bases or fewer, 300 bases or fewer, 200 bases or fewer, 150 bases or fewer, 100 bases or fewer or 50 bases or fewer.

If the motif region contains a plurality of stem-loop structures, in order to extract the motif region without segmenting it, a step of selecting one or more of the recognized stem structures in the RNA and a step of replacing the selected stem structure(s) by a putative loop structure(s) are preferably repeated with changing the stem structure(s) to be selected. In the present invention, the term "putative loop structure" is a structure in which the nucleic acid sequence inherently constituting the stem structure and the sequence complementary thereto are assumed not to hybridize with each other and exist as a single-stranded loop.

It is possible to accurately extract the motif region containing a plurality of stem-loop structures and forming a complicated higher-order structure, by changing the stem structure(s) to be selected and repeating the above steps.

Figure 2B:
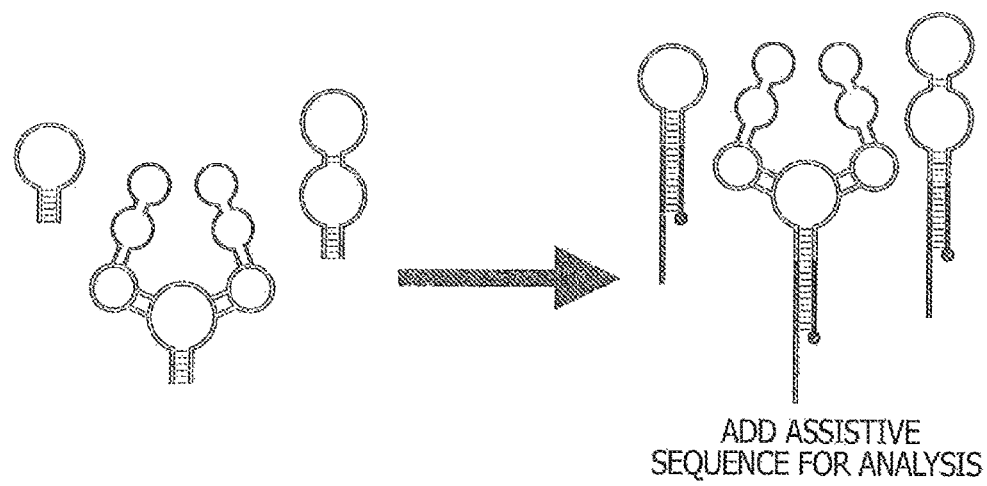
Figure 2C:
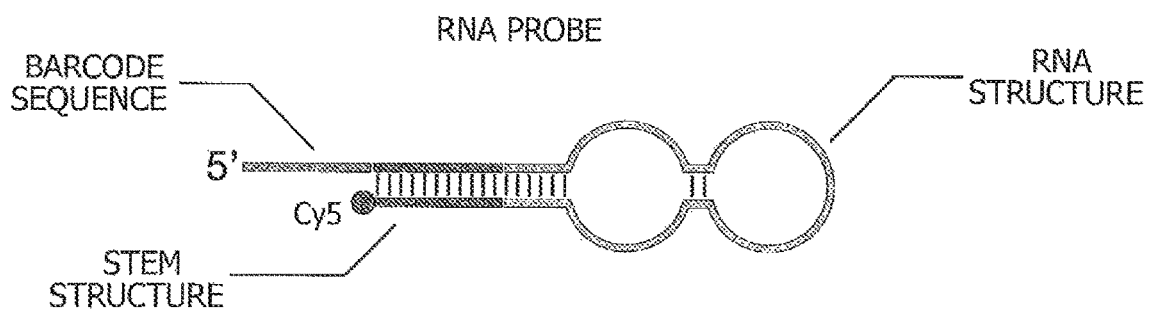

Then, a first assistive stem portion sequence and a second assistive stem portion sequence are added to the extracted motif region (FIGS. 2b and 2c). The first assistive stem portion and the second assistive stem portion hybridizes with each other to form a double-stranded assistive stem. The first assistive stem portion sequence may be any nucleic acid sequence, and the second assistive stem portion sequence may be any nucleic acid sequence so long as it is a sequence complementary to the first assistive stem portion sequence. For example, it is possible to use the sequence represented by SEQ ID NO: 2 as the first assistive stem portion sequence and the sequence represented by SEQ ID NO: 3 as the second assistive stem portion sequence, respectively. As described below, in the present invention, it is suitable to add a fluorochrome-labeled cytidine (3',5'-cytidine bisphosphate-Cy5 (pCp-Cy5)) to the 3' end of the RNA probe, and it is therefore desirable to add guanine (G) to the 5' end of the first assistive stem portion sequence. In the case of labeling a base other than cytidine (C) with a fluorochrome label, it is desirable to add another base which can be paired with the base to be labeled to the 5' end of the first assistive stem portion sequence.

In addition, a barcode region which represents a complementary sequence to a DNA barcode sequence is added to the assistive stem (FIGS. 2b and 2c). As the DNA barcode sequence of the present invention, it is possible to use tags (JP 1998-507357 A and JP 2002-518060 A), zip codes (JP 2001-519648 A) or normalized orthogonal sequences (JP 2012-181813 A), barcode sequences (Xu, Q. et al., Proc. Natl. Acad. Sci., Vol. 106, pp. 2289-2294, 2009), or the like. The DNA barcode sequence desirably has less cross-reactivity (cross-hybridization). In addition, the DNA barcode sequence preferably has a sequence of 20 to 30 bases, and particularly preferably 25 bases.

Once the sequence of the RNA probe of the present invention is determined by the above steps, the RNA probe can be synthesized by any genetic engineering technique conventionally known. Preferably, the RNA probe can be produced by transcribing a template DNA which has been synthesized by outsourcing to a synthesis outsourcee. For transcription of RNA from DNA, the DNA containing the sequence of the RNA probe may comprise a promoter sequence. Examples of the preferable promoter sequence include, but are not particularly limited to, a T7 promoter sequence. When the T7 promoter sequence is used, the RNA can be transcribed from the DNA encoding a desired RNA probe sequence by using MEGAshortscript™ T7 Transcription Kit provided by Life Technologies, for example. In the present invention, the RNA may be not only adenine, guanine, cytosine or uracil but also a modified RNA. Examples of the modified RNA include pseudouridine, 5-methylcytosine, 5-methyluridine, 2'-O-methyluridine, 2-thiouridine and N6-methyladenosine.

According to the method for preparing an RNA probe according to the present invention, the motif region can be incorporated in the RNA probe without being segmented, and the motif region in the RNA probe can therefore reproduce the higher-order structure existing in the RNA.

Accordingly, the present invention provides an RNA probe comprising the following regions (1) to (3):
(1) a barcode region which represents a complementary sequence to a DNA barcode sequence;
(2) an assistive stem region comprising a first assistive stem portion sequence and a second assistive stem portion sequence, wherein the second assistive stem portion sequence is a sequence complementary to the first assistive stem portion sequence and hybridizes to the first assistive stem portion sequence to form a double-stranded assistive stem; and
(3) a motif region which links the first assistive stem portion with the second assistive stem portion, the motif region comprising a sequence forming a higher-order structure having a multi-branched loop portion.

As the motif region contained in the RNA probe of the present invention, it is possible to use those extracted from any RNA sequence information according to the above-described method for preparing an RNA probe. Alternatively, as the motif region contained in the RNA probe of the present invention, it is possible to use those selected from any data on RNA secondary structures which have been already identified by RNA structurome research.

In the RNA probe of the present invention, the complementary sequence to the DNA barcode sequence is preferably a sequence which forms no base pair or pseudo-knot with the assistive stem region and/or the motif region. The sequence which forms no base pair or pseudo-knot with the assistive stem region and/or the motif region can be selected by using an RNA secondary structure prediction software such as IPknot (Sato, K. et al., Methods Biochem. Anal., Vol. 27, pp. i85-i93, 2011).

In the RNA probe of the present invention, the 5' end of the complementary sequence to the DNA barcode sequence is preferably a base other than uracil. This makes it possible to prevent variations in transcription efficiency from the template DNA into the RNA probe, and is therefore preferable when a plurality of RNA probes are synthesized simultaneously to prepare an RNA probe library.

The RNA probe of the present invention may be labeled with a fluorochrome (such as FITC, PE, Cy3 or Cy5), a radioactive isotope, digoxigenin (DIG), biotin or the like for detection. The RNA probe can be labeled by incorporating a previously labeled nucleic acid when synthesizing the probe, and can be labeled, for example, by fluorescently labeling cytidine (C) which is complementary to guanine (G) placed at the 5' side of the first assistive stem portion sequence (for example, pCp-Cy5) and incorporating it at the 3' end.

The present invention also provides an RNA probe library containing a plurality of the RNA probes, each containing a motif region having a different sequence. In the present invention, a microarray having the RNA probe is preferably prepared by preparing many types of RNA probes at the same time, and preferably efficiently by using a technique for synthesizing an oligo nucleic acid library containing RNA probes (oligonucleotide library synthesis technique). The oligonucleotide library synthesis can be performed by outsourcing to, but is not particularly limited to, Agilent Technologies.

The RNA probe library of the present invention can be provided as a kit for RNA analysis in combination with a microarray having DNA barcode sequences immobilized on a support. The kit for RNA analysis may include, as appropriate, an additional component such as a buffer solution, a container or instructions for use.

Alternatively, the RNA probe library of the present invention can be provided as an RNA microarray by hybridization thereof with a microarray having DNA barcode sequences immobilized on a support.

Examples of the support for immobilizing DNA barcode sequences thereon as used in the present invention include a semiconductor such as silicon, an inorganic substance such as glass or diamond or a film containing as a major component a polymeric material such as polyethylene terephthalate or polypropylene. Also, examples of the shape of the substrate include, but are not limited to, a microscope slide, a microwell plate, a microbead or a fiber.

Examples of the process for adding DNA barcode sequences to a support include, but are not limited to, a process comprising previously introducing a functional group such as an amino group, an aldehyde group, an SH group or biotin into a nucleic acid having a DNA barcode sequence while introducing a functional group capable of reacting with the nucleic acid (such as an aldehyde group, an amino group, SH group or streptavidin) into a support, and then crosslinking the immobilizing support and the nucleic acid by a covalent bond between both functional groups; or a process comprising coating the immobilizing support with a polycation and immobilizing an polyanionic nucleic acid thereon with aid of electrostatic binding. The process for preparing a DNA barcode sequence may be the Affymetrix method, in which a nucleic acid probe is synthesized by synthesizing nucleotide by nucleotide on a substrate (such as glass or silicon) using a photolithographic approach, or may be the Stanford method, in which a nucleic acid having a DNA barcode sequence previously prepared is spotted on a substrate using a microspotting, an inkjet process, a Bubble Jet® process or the like. The Stanford method or a technique comprising a combination of the both methods is preferable when using a probe of 30 mer or more. The immobilizing support having the DNA barcode sequences added thereto can be produced by outsourcing to an outsourcee.

In the RNA probe library of the present invention, RNA probes can specifically bind to a support by hybridizing with a microarray of DNA barcode sequences immobilized on the support. Hybridization can be performed by changing, as appropriate, the salt concentration of a solution for hybridization, temperature, probe concentration, reaction time, salt concentration of a washing solution, washing temperature or the like.

The RNA probe libraries of the present invention can be spotted on the same single support (for example, a glass slide having a size of 1 inch by 3 inches) to provide an RNA microarray having RNA probes at a density similar to that of a DNA microarray such as 500 or more, 1000 or more, 2000 or more, 3000 or more, 4000 or more, 5000 or more, 10000 or more probes/microarray.

If any protein is subjected to the RNA microarray of the present invention in a solvent, the RNA probe which binds to the protein can be detected. In this case, the solvent may be, for example, an aqueous solution containing 20 mM Tris-HCl, 300 mM NaCl, 5 mM of $MgCl_2$ and 0.1% Tween-20 or the like. The concentration of a target protein to be subjected to a microarray may be 5 nM, 10 nM, 20 nM, 30 nM, 40 nM, 50 nM, 60 nM, 70 nM, 80 nM, 90 nM or 100 nM, and preferably is 40 nM or less. For the detection of protein binding, the protein may be labeled with a fluorochrome (such as FITC, PE, Cy3 or Cy5), a radioactive isotope, digoxigenin (DIG), biotin or the like. Also, the label for the protein is preferably different from a label for the RNA probe. For example, it is possible to label the RNA probe with Cy5 and label the protein with Cy3.

The present invention also provides a method for detecting an RNA which binds to a protein, comprising the following steps:
(1) contacting the RNA probe according to any one of claims [3] to [6] with a target protein;
(2) isolating a conjugate of the RNA probe obtained in the step (1) and the target protein;
(3) extracting the RNA probe from the conjugate isolated in the step (2),
(4) contacting the RNA probe extracted in the step (3) with a microarray having DNA barcode sequences immobilized on a support;
(5) identifying the RNA probe hybridized with one of the DNA barcode sequences in the step (4); and
(6) detecting an RNA containing a sequence of a motif region of the RNA probe identified in the step (5) as the RNA which binds to the target protein.

In the method of the present invention, the RNA probe is contacted with the target protein. This step can be performed under the same conditions as those for binding between the RNA microarray and the protein as mentioned above. The amount of the RNA probe used in this step may be 100 μg or less and is preferably 1 μg. The amount of the target protein used in this step may be 1 pmol, 2 pmol, 3 pmol, 4 pmol, 5 pmol, 10 pmol, 20 pmol, 30 pmol, 40 pmol, 50 pmol, 60 pmol, 70 pmol, 80 pmol, 90 pmol or 100 pmol, and preferably is 20 pmol or less.

Then, a conjugate of the RNA probe and the target protein are isolated. In order to make it easy to isolate the conjugate, the target protein may be bound to a carrier such as a resin or a magnetic bead. In order to bind the target protein to the carrier, the carrier may be preferably crosslinked or coated with Protein A, Protein G or Protein L, a metal ion (such as an ion of copper, nickel, zinc or cobalt), biotin, glutathione or the like. In order to bind the target protein to the carrier, the target protein may be tagged with a His tag or GST tag, or an antibody specific to the target protein may be used.

Then, the RNA probe is extracted from the isolated conjugate. The RNA probe can be extracted by any method for extracting a nucleic acid that is conventionally known.

Then, the extracted RNA probe is contacted with a microarray having DNA barcode sequences immobilized on a support, and the RNA probe hybridized with the DNA barcode sequences is identified. This step can be performed in a manner similar to that described above.

The RNA probe of the present invention contains a motif region without being segmented, and reflects the function of the original RNA. Therefore, according to the present invention, the RNA containing the sequence of the motif region of the RNA probe hybridized with the DNA barcode sequence can be detected as the RNA which binds to the target protein.

Examples

The present invention will be further described with reference to examples described below, but will not be limited by these examples in any way.

Example 1. Construction of RNA Structure Library

An RNA structure library for human 5' UTR and an RNA structure library for the HIV-1 genome were produced according to the following procedures.

1-1. Production of Human 5' UTR RNA Structure Library

A. Selection of RNA Structure Sequence

All sequence information of human 5' UTR registered in UTRdb (Grillo, G. et al., Nucl. Acids Res., Vol. 38, D75-D80, 2010) was downloaded. In consideration of the accuracy of RNA secondary structure prediction and the cost and level of difficulty in producing reporter mRNAs in the following validation experiments, only sequences having a total length of 5' UTR of 400 nucleotides or fewer were selected. The secondary structure of RNA was predicted for the selected sequences. The software used was CentroidFold (Hamada, M. et al., Bioinformatics, Vol. 25, pp 465-473, 2009). The option-gamma was set to 4.

The secondary structure of RNA was recognized by the following algorithm:
(1) The hairpin loop structures contained in the secondary structure predicted from the inputted RNA sequence are recognized.
(2) The RNA structure around the recognized hairpin loop structure is segmented. This operation is repeated for all hairpin loop structures recognized. As a result, when n hairpin loop structures are recognized, n+1 RNA fragments are formed (wherein n is a natural number).
(3) The n-th hairpin loop structure is focused on. The n-th hairpin loop structure consists of the n-th RNA fragment comprising a first stem portion and the (n+1)-th RNA fragment comprising a second stem portion which is complementary to the first stem portion. That is, an RNA structure having a stem structure at the end is selected by binding the n-th RNA fragment to the (n+1)-th RNA fragment. This structure is recorded.
(4) The double-stranded structure (stem portion) in the selected RNA structure is replaced with a single-stranded structure (putative loop).
(5) The above operations (1) to (4) are repeated.
(6) The portion replaced with the single-stranded structure is returned to the double-stranded structure. This allows an RNA structure having a multi-branched loop to be selected.
(7) The stem structure is shortened so that it falls within the upper size limit (116 bases) of the library.

In order to adjust the scale of the library, RNA structures contained in the library was screened so that the total number of RNA structures was 9,000 or fewer according to the following criteria:
(1) Information of sequences conserved across species was obtained from UTRdb.
(2) Among the sequences conserved across species, those that do not overlap with the selected RNA structure sequences were excluded.
(3) The position coordinates of the sequence were defined. The 5' end of the RNA structure is designated as L, the 3' end of the RNA structure is designated as R, the 5' end of the sequence conserved across species is designated as Lc, and the 3' end the sequence conserved across species is designated as Rc. These values are expressed as numerical values counted from the 5' end of the original 5' UTR sequence.
(4) When the RNA structure sequence is longer than the sequence conserved across species: it is adopted if $L <= Lc+2$ bases and $Rc-2 <= R$ and $(Rc-Lc)/(R-L)$ is greater than 0.13.
(5) When the RNA structure sequence is shorter than the sequence conserved across species: it is adopted if $Lc <= L+4$ bases and $R-4$ bases $<= Rc$ and $(R-L)/(Rc-Lc)$ is greater than 0.5865.

(6) When the RNA structure sequence is equal to the sequence conserved across species: it is adopted when Lc<=L+4 bases and R−4 bases<=Rc and (Rc−Lc)/(R−L) is greater than 0.13.

(7) The RNA structures finally selected included RNA structures, having known functions of interacting with eIF3 in cells, present in the IRE (Iron response element) and 5' UTR of BTG1.

(8) The RNA structures to which RNA-binding proteins such as LIN28A, MS2, Roquine, L7Ae and U1A bind were adopted as positive controls in the remaining frame of the library.

B. Preparation of RNA Probe

An RNA probe was prepared by adding an assistive sequence for analysis in the microarray to an RNA left after screening. The RNA probe was prepared by in vitro transcription of a template DNA. The template DNA was designed so as to comprise, from the 5' end in order, (i) CC+T7 promoter+G (24 bases), (ii) barcode sequences (25 bases), (iii) G+Stem forward sequence (18 bases), (iv) an RNA structure sequence (6 to 116 bases), and (v) Stem reverse sequence (17 bases).

(i) CC+T7 promoter+G (24 bases)

```
                                             (SEQ ID NO: 1)
5'-CCGCGCTAATACGACTCACTATAG-3'
```

(ii) barcode sequences (25 bases)

The barcode sequences used were selected from sequences left after excluding, sequences having U as the first base form the 5' end, from 240,000 DNA sequences of 25-mer bases disclosed in the prior art reference (Xu, Q. et al., Proc. Natl. Acad. Sci., Vol. 106, pp. 2289-2294, 2009), based on the following criteria (1) to (3). Three types of barcode sequences were selected and used for each RNA structure sequence. By using three different barcode sequences, the effect of the barcode sequence on binding of the RNA structure sequence to a protein and the effect of the hybridization efficiency on the fluorescence intensity can be considered by the statistical processing comprising:

(1) applying IPknot (option: -g4 -g8) to the RNA sequence having an assistive sequence added to the RNA structure sequence.
(2) confirming that the RNA structure sequence and the barcode sequences form no base pair or pseudo-knot; and
(3) confirming that the barcode sequences and Stem forward sequence form no base pair or pseudo-knot.

(iii) G+Stem forward sequence (18 bases)

```
                                             (SEQ ID NO: 2)
5'-GGTGTACGAAGTTTCAGC-3'
```

(iv) RNA structure sequence (6 to 116 bases)
The sequence selected by the above algorithm was used.
(v) Stem reverse sequence (17 bases)

```
                                             (SEQ ID NO: 3)
5'-GCTGAAGCTTCGTGCAC-3'
```

The single-stranded template DNA designed as above was synthesized by outsourcing to Agilent Technologies. The template DNA was appropriately amplified by PCR using Library forward Primer (SEQ ID NO: 4) and Library reverse Primer (SEQ ID NO: 5). The single-stranded template DNA was subjected to a transcription reaction in an in vitro transcription system (MEGAshortscript™T7 Transcription Kit, Thermo Fisher Scientific) to prepare an RNA probe. 20 µL of a reaction solution (1×T7 Reaction Buffer, 7.5 mM GTP solution, 7.5 mM ATP Solution, 7.5 mM CTP Solution, 7.5 mM UTP Solution, 1×T7 Enzyme Mix, 37.5 nM of the template single stranded DNA, 2.5 µM CC-T719-G ssDNA (5'-CCGCGCTAATACGACTCACTATAG-3': SEQ ID NO: 1)) was incubated at 37° C. for 20 hours. Thereafter, 2 µL of TURBO DNase (Thermo Fisher Scientific) was added to the reaction solution, mixed and incubated at 37° C. for 15 minutes. 15 µL of an ammonium acetate stop solution (5 M ammonium acetate, 100 mM EDTA) was added thereto to stop the reaction. The obtained reaction liquid was purified with the RNeasy MinElute Cleanup Kit (QIAGEN) to finally obtain a little less than 30 µL of an RNA probe solution. C. Cy5 fluorescence labeling of RNA probe pCp-Cy5 (Jena Bioscience) was added to the 3' end of the RNA probe with T4 RNA ligase (Thermo Fisher Scientific). The RNA probe labeled with Cy5 was purified using RNeasy MinElute Cleanup Kit (QIAGEN). The RNA concentration was determined by measuring the absorbance at 260 nm and the labeled Cy5 concentration was determined by measuring the absorbance at 650 nm. Each measurement was performed with NanoDrop 2000 (Thermo Fisher Scientific).

D. Design of Custom Array Spotted with 25 mer DNA Barcode

A single-stranded DNA complementary to the barcode sequence added to each RNA probe was prepared and spotted on the CGH custom array 8×60K (Agilent). Two RNA spots were placed for each RNA probe.

E. Scanning of RNA Structure Library with DNA Microarray 16 ng of the Cy5-labeled RNA probe was dissolved in 18 µL of ultrapure water, 4.5 µL of 10× Blocking Agent (Agilent) and 22.5 µL of RPM Hybridization Buffer (Agilent) were added thereto, and they were mixed. The mixture was incubated on a heat block at 104° C. for 5 minutes and then on ice for 5 minutes. The total amount of the reaction liquid was applied to an 8×60K Agilent microarray gasket slide (Agilent). The hybridization chamber (Agilent) was fitted with the gasket slide and a CGH custom array 8×60K (Agilent), and placed in a hybridization oven (Robbins Scientific) previously warmed to 55.5° C., and hybridization process was thereby performed at 20 rpm for 20 hours. The gasket slide was removed, washed with Gene Expression Wash Buffer 1 (Agilent) at room temperature for 5 minutes and with Gene Expression Wash Buffer 2 (Agilent) at 37° C. for 5 minutes. Image data was obtained with the slide fitted in the slide holder by using SureScan (Agilent) at a setting of Agilent G3_GX_2color. Data on fluorescence intensity for each spot was obtained by the software Feature Extraction (Agilent). The data was analyzed with Gene Spring (Agilent) as well as the scripts written in Python and Julia. The fluorescence of Cy5 was confirmed to be detected from the spot of the barcode sequence corresponding to the RNA probe, and the RNA probe was thereby confirmed to be bound to the spot corresponding thereto.

1-2. Production of RNA Structure Library of HIV-1 Genome

An RNA structure library of the HIV-1 genome was prepared in a manner similar to in 1-1 except that the HIV-1 genome was used instead of the human 5' UTR. The RNA structure data of the HIV-1 genome used was data analyzed by SHAPE-MaP (Siegfried, N. A. et al., Nat. Methods, Vol. 11, pp. 959-965, 2014). Using the algorithm "RemovePseudoKnots" published in the website RNA Structure by the University of Rochester Medical Center, the RNA structure information is converted into secondary structure information without considering any pseudo-knots, and further converted into dot-bracket format by the algorithm "ct2dot" published on the same website.

Example 2. Analysis of LIN28A-Binding RNA Sequence by RIP-Chip Method

LIN28A-binding RNA sequence was analyzed by RIP-Chip method using the RNA structure libraries for the human 5'UTR and the HIV-1 genome.

2-1. RNA Immunoprecipitation

20 µL of TALON Magnetic beads (Clontech), 20 pmol of the His-tagged purified LIN28A protein and 1 µg of Cy5-RNA probe were mixed in 500 µL of Protein Binding Buffer (20 mM Hepes pH 7.8, 80 mM KCl, 20 mM NaCl, 10% glycerol, 2 mM DTT, 0.2 µg/µL BSA). Then, the mixture was stirred at 4° C. for 30 minutes with MACSmix Tube Rotator (Miltenyi Biotec). Thereafter, TALON Magnetic beads were retained with 12-Tube Magnet (QIAGEN), and the solution was removed. After washing TALON Magnetic beads three times with Protein Binding Buffer, 200 µL of Elution Buffer (1% SDS, 10 mM Tris-HCl, 2 mM EDTA) was added thereto and incubated at 95° C. for 3 minutes to elute the LIN28A protein-RNA.

2-2. Extraction and Purification of RNA

200 µL of Phenol:Chloroform:Isoamyl Alcohol 25:24:1 Mixed, pH 5.2 (Nacalai Tesque) was added to the above solution, suspended therein, and then centrifuged at 20,400× g at 4° C. for 5 minutes to collect approximately 150 µL of an aqueous layer. 150 µL of chloroform was added to the collected aqueous layer, suspended therein, and then centrifuged at 20,400× g at 4° C. for 5 minutes to collect approximately 100 µL of an aqueous layer. 200 µL of 100% ethanol, 1 µL of Ethachinmate (Nippon Gene) and 3.3 µL of 3 M sodium acetate were added to the collected aqueous layer, and was incubated at −80° C. for 15 minutes and then centrifuged at 20,400× g at 4° C. for 15 minutes to isolate RNA. The isolated RNA was rinsed with 80% ethanol and then dried, and was dissolved in 20 µL of ultrapure water.

2-3. Scanning of RNA Structure Library for Human 5' UTR with DNA Microarray Using 18 µL of the obtained RNA solution, scanning was performed with a microarray according to the procedure similar to that used in 1-1-E above. Some of the results are shown in Table 1. For known LIN28A-binding RNAs, the loop structure of pre-miRNA of hsa-let-7d (SEQ ID NO: 6) (rank 15) and the loop structure of pre-miRNA of hsa-mir-98 (SEQ ID NO: 7) (rank 5) were detected in higher ranks. On the other hand, the loop structure of the pre-miRNA of hsa-let-7a-3, which is known not to bind to LIN28A, (SEQ ID NO: 8) was detected in a very low rank (rank 6278). These results show that the binding capacity of the RNA structure to LIN28A can be evaluated normally by this method.

Table 1. Ranking of binding affinity to LIN28A

TABLE 1

| Rank | Name | Cy5 Intensity |
|---|---|---|
| 1 | BA085801_1 | 7.84 |
| 2 | BA047565_1_Multi | 7.75 |
| 3 | BA060819_1 | 7.63 |
| 4 | BA118290_1 | 7.55 |
| 5 | pre-hsa-mir-98 | 7.53 |
| 6 | pre-hsa-mir-940 | 7.50 |
| 7 | BA109612_1 | 7.50 |
| 8 | BA032435_1 | 7.46 |
| 9 | BA018470_1 | 7.42 |
| 10 | hsa-mir-532 | 7.39 |
| 11 | BA105829_1 | 7.38 |
| 12 | BA051648_1 | 7.36 |
| 13 | BA038726_Muiti | 7.34 |
| 14 | BA111275_1 | 7.31 |
| 15 | pre-hsa-let-7d | 7.30 |
| — | — | — |
| 6278 | pre-hsa-let-7a-3 | 4.31 |

2-4. Motif Analysis with RBP Motifs

Figure 3A:
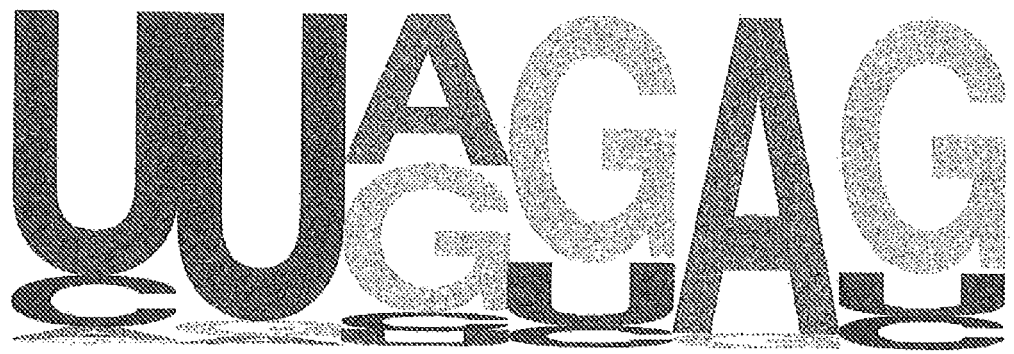
FIG. 3 is a diagram showing the results of structural analysis of the LIN28A-binding motifs.
Figure 3B:
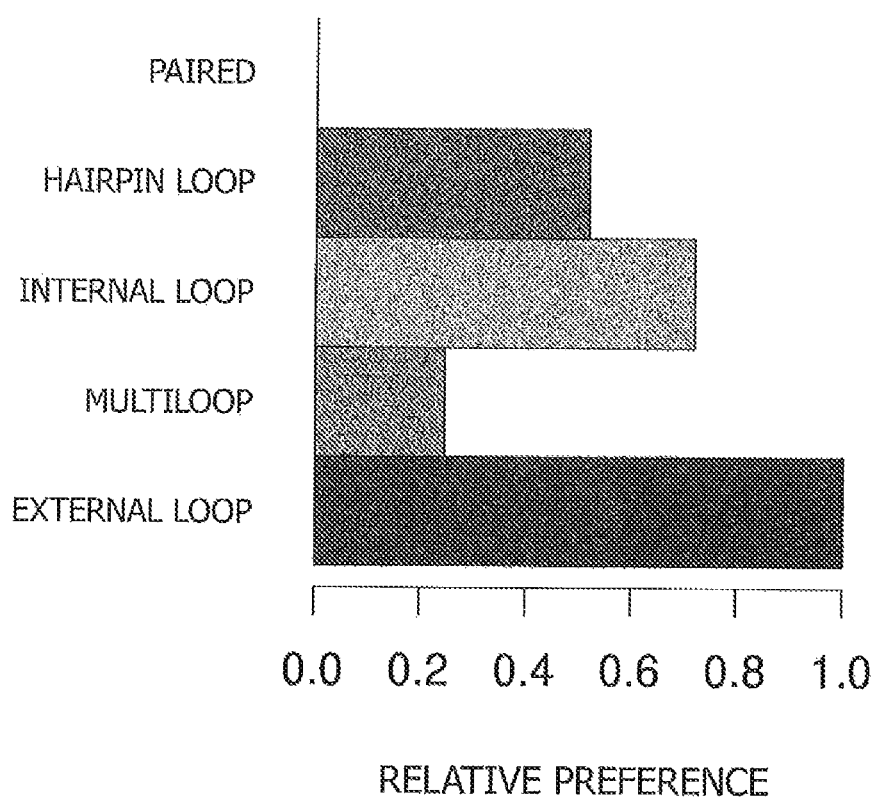

Motif analysis was performed by entering, into the RBPmotif web server, the RNA sequences ranked the highest 100 and the RNA sequences ranked the lowest 500 in ranking of the binding affinity to LIN28A. Results are shown in FIG. 3. As binding motifs similar to the known LIN28A-binding motifs, for example, GGAG and the like were obtained (FIG. 3a). In addition, many of these motifs were revealed to exist in the single-stranded region (FIG. 3b).

2-5. Binding Affinity of Novel Discovered RNA Structure to LIN28A

Figure 4:
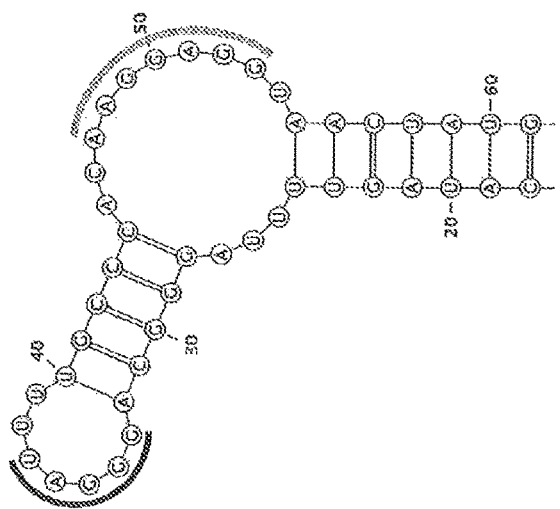
FIG. 4 is a diagram showing the structures of novel and known LIN28A-binding motifs.
Figure 4:
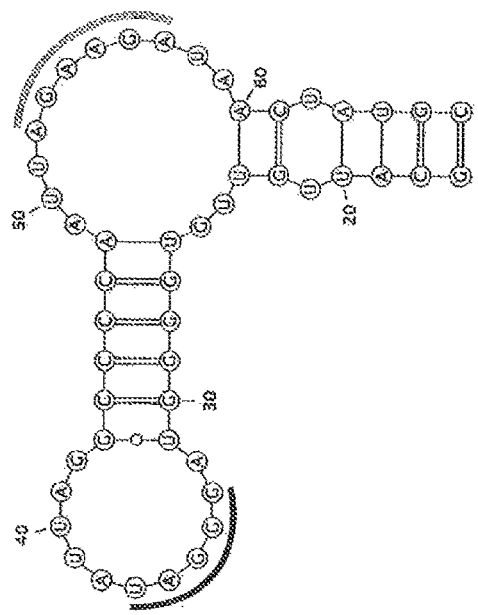
Figure 4:
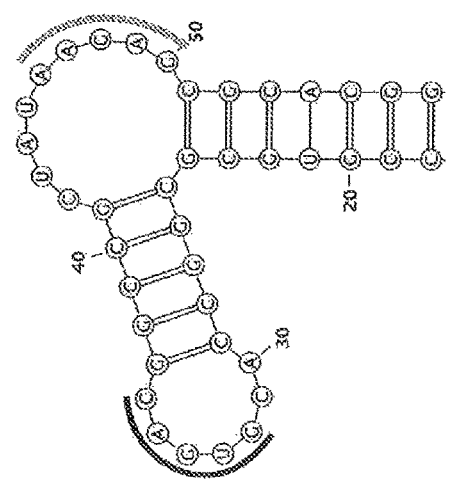

The RNA structure (SEQ ID NO 9) ranked in rank 2 obtained in 2-3 above was focused on. This structure is an RNA structure contained in the 5' UTR of GYG 1 (hereinafter referred to as Rank2-GYG1, FIG. 4a). Rank2-GYG1 was revealed to be similar in both sequence and structure to the pre-miRNA loop of hsa-let-7d (FIG. 4b) and the pre-miRNA loop of hsa-mir-98 (FIG. 4c). The binding affinity of Rank2-GYG1 to LIN28A was confirmed by EMSA (Electrophoresis Mobility Shift Assay). First, RNA probes having stem structures added to Rank2-GYG1, the loop structure of the hsa-mir-98 precursor, the loop structure of the hsa-let-7d precursor and the loop structure of the hsa-let-7a-3 precursor was designed. A CC+T7 promoter sequence was added to the 5' end of each of these sequences, and the complementary strand thereto was synthesized as a template single-stranded DNA (by outsourcing to Greiner). In vitro transcription synthesis was performed using T7-19mer (synthesized by outsourcing to Greiner) by the procedure similar to that in 1-1-B above.

EMSA was performed according to the following procedure. An RNA solution was incubated at 95° C. for 5 minutes and then at room temperature for 10 minutes. Next, a reaction liquid (100 nM RNA, 1.2, 0.6, 0.3 and 0 µM LIN 28 A, 1× Protein Binding Buffer (20 mM Hepes pH 7.8, 80 mM KCl, 20 mM NaCl, 10% glycerol, 2 mM DTT, 0.2 µg/µL BSA)) was prepared and incubated at room temperature for 60 minutes. After reacting them, 1.2 µL of 10× loading dye (0.25% bromophenol blue, 30% glycerol) was added thereto and mixed. After pre-running at 15 mA for 5 minutes, the mixture liquid was applied to a non-denaturing 10% polyacrylamide gel and electrophoresis was performed at 15 mA for 30 minutes. The gel after electrophoresis was stained with SYBR Green I and II. It was imaged with Gel Doc EZ (Bio-Rad) and the bands were confirmed.

Figure 5:
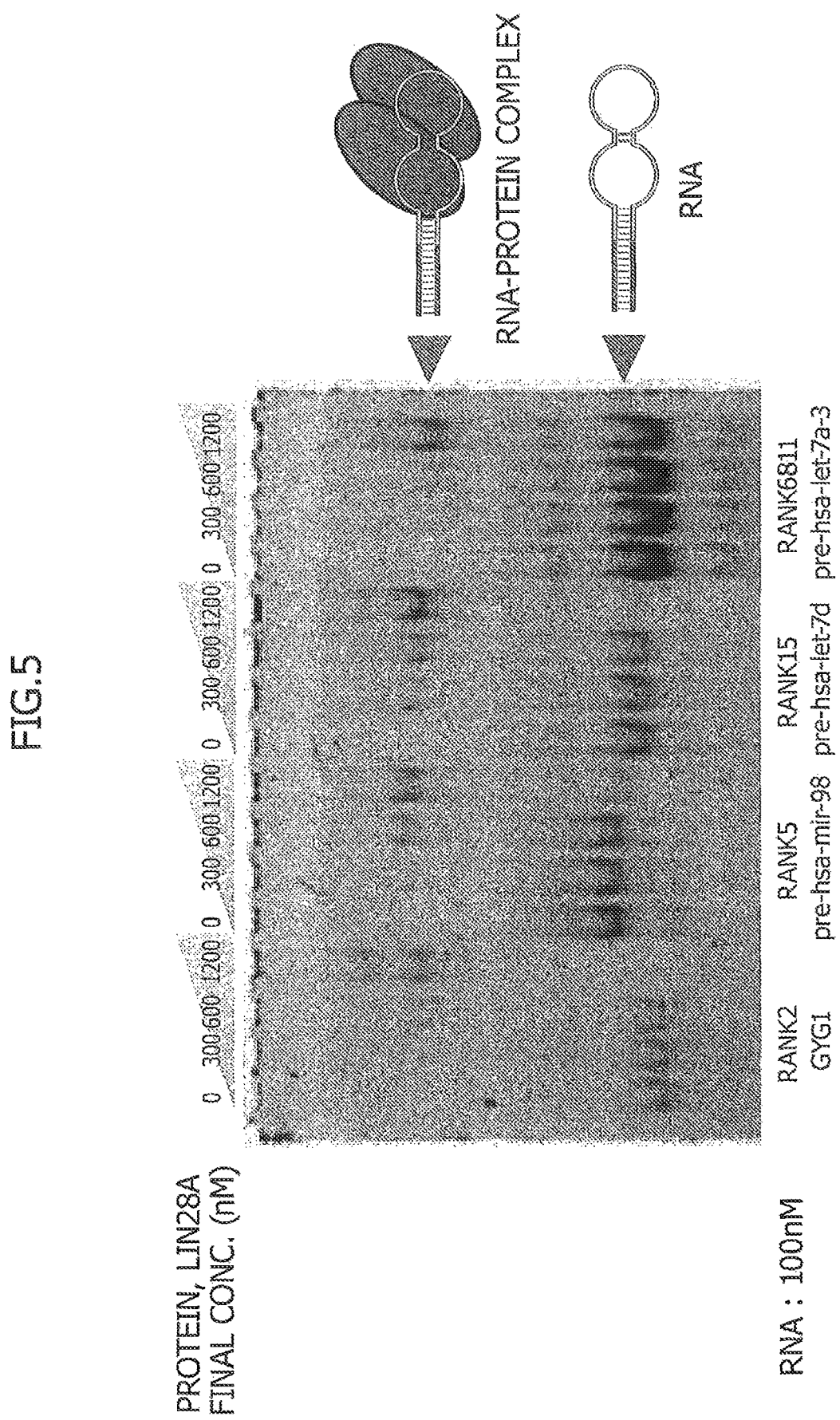
FIG. 5 is a diagram showing the results of a gel shift assay for evaluating the LIN28A-binding affinities of the novel LIN28A-binding motifs.

The results are shown in FIG. 5. Judging the binding strength based on the extent of regression of the unbound RNA band, it was clear that Rank2-GYG1 bound to LIN 28 A with strong affinity.

Example 3. Analysis of eIF3b-Binding RNA Sequence by RIP-Chip Method

Analysis of eIF3b-binding RNA sequence was performed using an RNA structure library for human 5' UTR and an RNA structure library for HIV-1 genome by RIP-Chip method.

3-1. Preparation of Cell Lysate

HEK293FT cells were seeded in a culture medium in a 10 cm dish at a concentration of $1.0 \times 10^5$ cells/mL. After culturing them for 48 to 72 hours, the culture medium was removed and the cells were washed with PBS. After addition of 5 mL of PBS, the cells were peeled off with a cell scraper and collected in a 50 mL tube. After centrifugation at 300× g at 4° C. for 5 minutes, the supernatant was removed. By adding ice-cold PBS to the cell pellet, the cell pellet was resuspended therein and centrifuged at 300× g at 4° C. for 5 minutes, and a supernatant was removed to obtain a cell pellet. 10 mL of a cell lysis buffer (9 mL of NP-40 Cell Lysis buffer (Thermo Fisher Scientific), 1 mL of Protease Inhibitor Cocktail (SIGMA), 174.2 µL of PMSF) was added to the cell pellet and incubated on ice for 30 minutes. During this incubation, it was vortexed for 10 seconds every 10 minutes. Thereafter, it was centrifuged at 13,000 rpm at 4° C. for 10 minutes. A supernatant was collected and cryopreserved at −80° C.

3-2. Co-Immunoprecipitation and Western Blotting

Co-immunoprecipitation was performed by mainly using Dynabeads Protein A Immunoprecipitation Kit (Thermo Fisher Scientific) according to the procedure pursuant to the protocol recommended by the manufacturer. 15 µL of resuspended Dynabeads was dispensed into 1.5 mL tubes, and each of tubes was placed in a magnetic rack to remove the supernatant. 200 µL of Ab Binding Buffer and 20 µL of rabbit anti-eIF3b antibody (Bethyl, 0.2 mg/mL) were added thereto and stirred at room temperature for 13 minutes with a tube rotator. Each of the tubes was placed in the magnetic rack to remove a supernatant, and 200 µL of Binding/Washing Buffer included in the Kit was added thereto to wash the Dynabeads-antibody complex. The Buffer was removed, 1000 µL of the collected cell lysate (700 µg/µL) was added to the complex, and the mixture was stirred at 4° C. for 1 hour with a tube rotator. Each of the tubes was placed in the magnetic rack to remove a supernatant, and the Dynabeads-antibody-binding protein complex was washed three times with Washing Buffer. 20 µL of Elution Buffer and 20 µL of 6×SDS Sample Buffer (Nacalai Tesque) containing a reducing agent were added thereto, and incubated at 95° C. for 5 minutes and at room temperature for 15 minutes. The Dynabeads were removed to collect a supernatant.

The collected sample was electrophoresed on SDS-PAGE, and the protein was then transferred to a polyvinylidene fluoride (PVDF) membrane using iBlot (Thermo Fisher Scientific). The PVDF membrane after transcription was incubated overnight in Blocking One (Nacalai Tesque) and then incubated for 1 hour at room temperature in TBS-T (200 mM NaCl, 20 mM Tris-HCl, 0.5% Tween) having a primary antibody added thereto. The primary antibody used was a rabbit anti-eIF3a antibody (Bethyl) (1:1000 dilution), a rabbit anti-eIF3b antibody (Bethyl) (1:2000 dilution) or a rabbit anti-eIF3d antibody (Bethyl) (1:1000 dilution). Thereafter, the antibody liquid was removed, and the residue was washed four times with TBS-T and incubated at room temperature for 30 minutes in TBS-T having a secondary antibody added thereto. The secondary antibody used was a goat anti-rabbit IgG (H+L)-HRP complex (Bio-Rad) (1:2000 dilution). Thereafter, the antibody liquid was removed, the residue was washed four times with TBS-T, and the protein was then detected with ECL Prime Western Blotting Detection Reagent (GE Healthcare) and LAS 4000 (GE Healthcare).

Figure 6A:
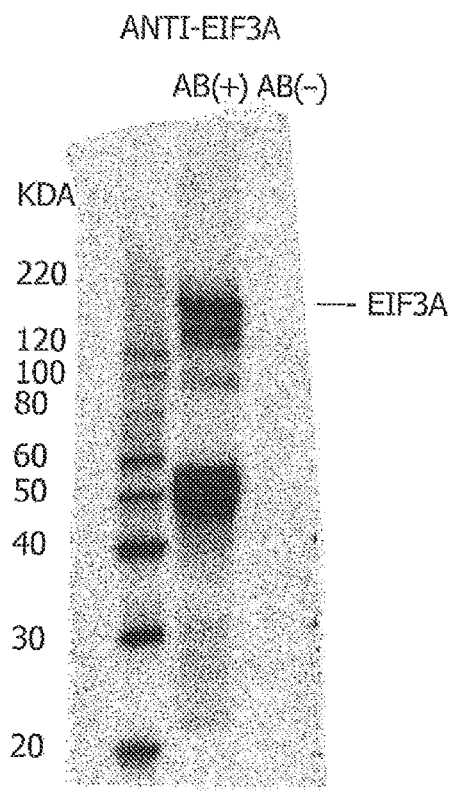
FIG. 6 is a diagram showing the results of co-immuno-precipitation performed with an anti-eIF3b antibody in a cell suspension obtained from HEK293FT cells.
Figure 6B:
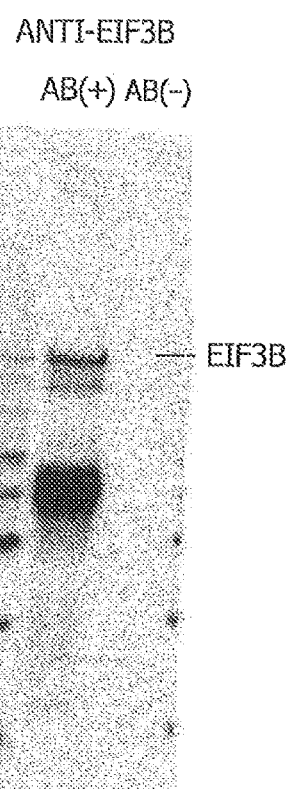
Figure 6C:
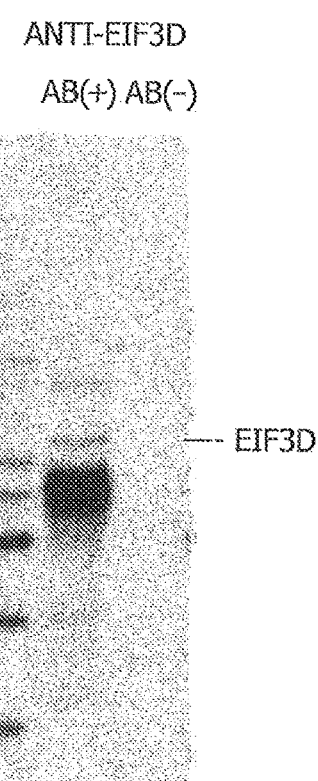

The results are shown in FIG. 6. It was confirmed that all of eIF3a, eIF3b and eIF3d were detected and that eIF3b bound to eIF3a and eIF3d. From these results, it was determined that the eIF3 complex obtained by the above procedure could be used for detecting RNA structures which binds to eIF3a, eIF3b or eIF3d.

3-3. RNA Co-Immunoprecipitation and Extraction and Purification of RNA

Dynabeads-antibody-eIF3 complex was obtained according to the procedures similar to those in 3-1 and 3-2 above. After washing the complex with 1 mL of RNP Binding Buffer (20 mM Hepes pH 7.8, 80 mM KCl, 20 mM NaCl, 10% glycerol, 2 mM DTT, 0.2 µg/µL BSA), 500 µL of RNP Binding Buffer and 500 ng of a Cy5-labeled RNA probe was added thereto and the mixture was stirred at 4° C. for 1 hour with a tube rotator. Tubes were placed in a magnetic rack to remove a supernatant, and the residue was washed three times with 500 µL of RNP Binding Buffer. 200 µL of Elution Buffer (1% SDS, 10 mM Tris-HCl, 2 mM EDTA) was added thereto and incubated at 95° C. for 3 minutes to elute eIF3 complex-RNA. Thereafter, a purified RNA solution was prepared according to the procedure similar to that in 2-2 above.

3-4. Scanning of RNA Structure Library with DNA Microarray

Using 18 µL of the obtained RNA solution, scanning was performed with a microarray according to the procedure similar to that in 1-1-E above.

3-5. Data Analysis: Calculation for RNA Secondary Structure Prediction and of Minimum Free Energy of its Structure Using the software RNAfold included in ViennaRNA package 2.2.5, the secondary structure of the RNA and the minimum free energy of its structure were calculated.

Figure 7A:
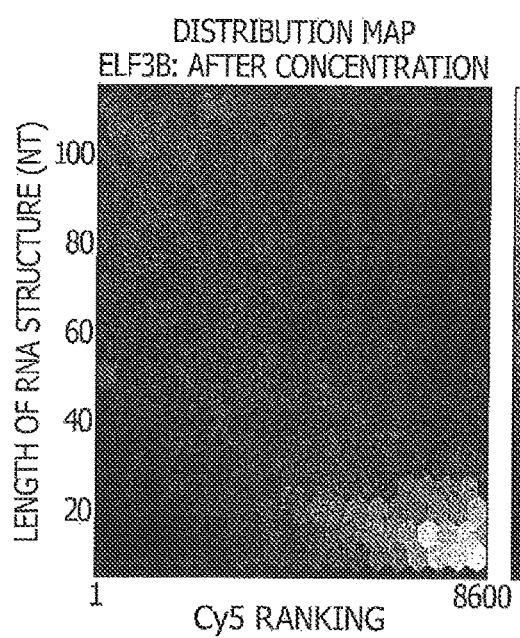
FIG. 7 is a diagram showing the tendency of the RNA structures concentrated by co-immunoprecipitation with anti-eIF3b antibody.
Figure 7B:
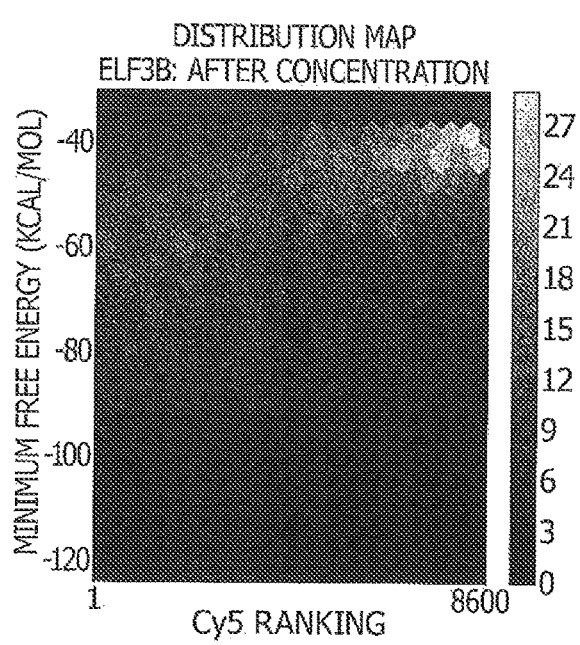
Figure 8A:
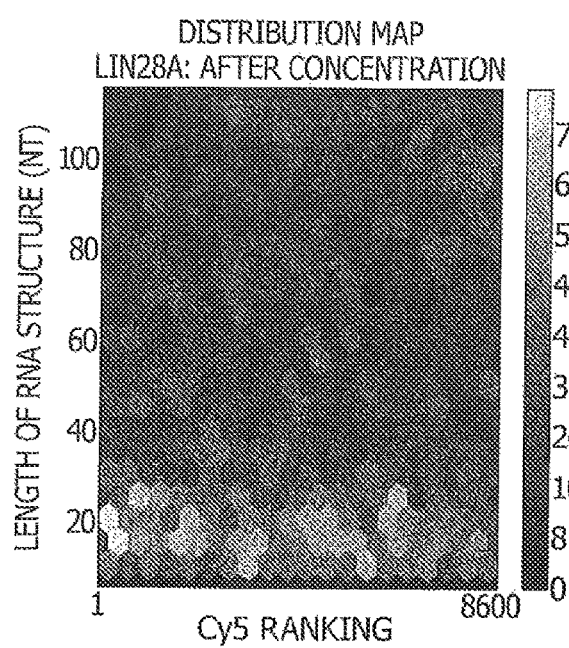
FIG. 8 is a diagram showing the tendency of the RNA structures concentrated by immunoprecipitation with LIN28A.
Figure 8B:
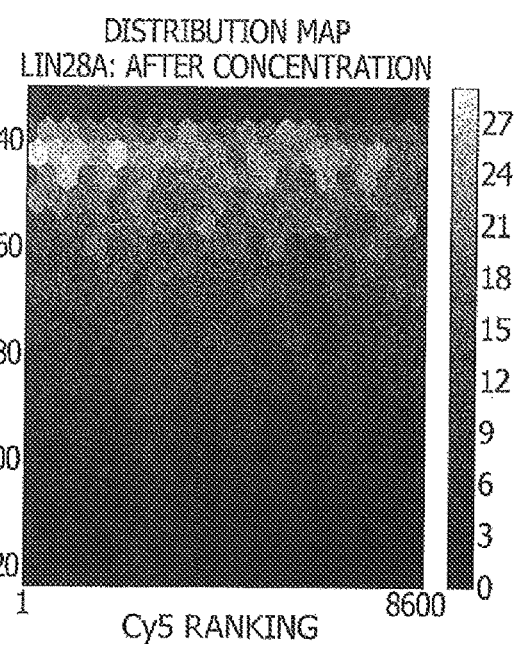

The results are shown in FIG. 7. From these results, it was shown that many of RNAs which bind to the eIF3 complex had many long bases (FIG. 7a) and that many of them had a low minimum free energy and formed double-stranded structures in the molecules (FIG. 7b). This is completely different from the tendency seen in the RNAs which bind to LIN28A obtained in Example 2 (FIG. 8).

Figure 9:
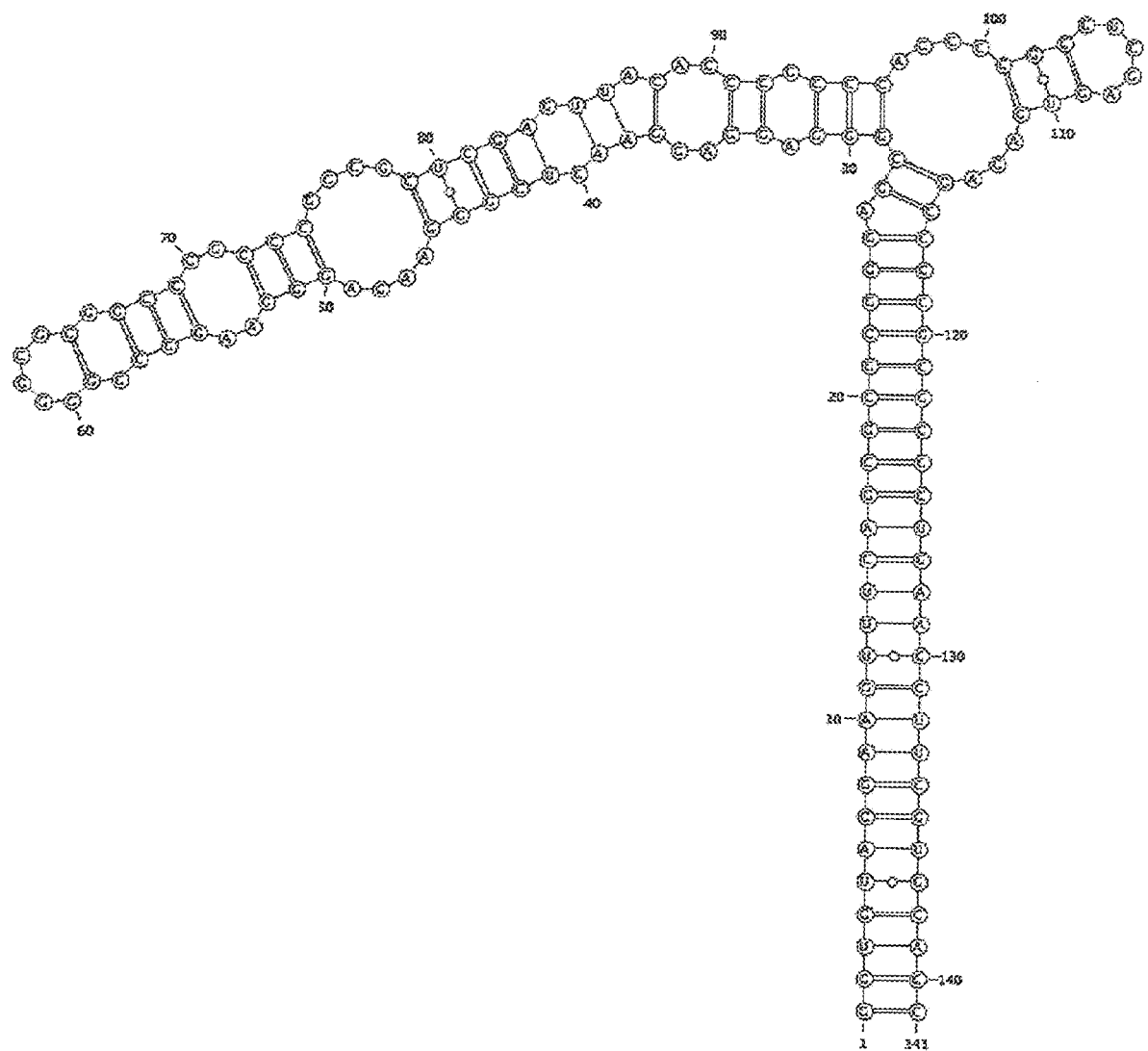
FIG. 9 is a diagram showing the secondary structures of RNAs ranked higher in ranking of the binding affinity to eIF3 complex.
Figure 9:
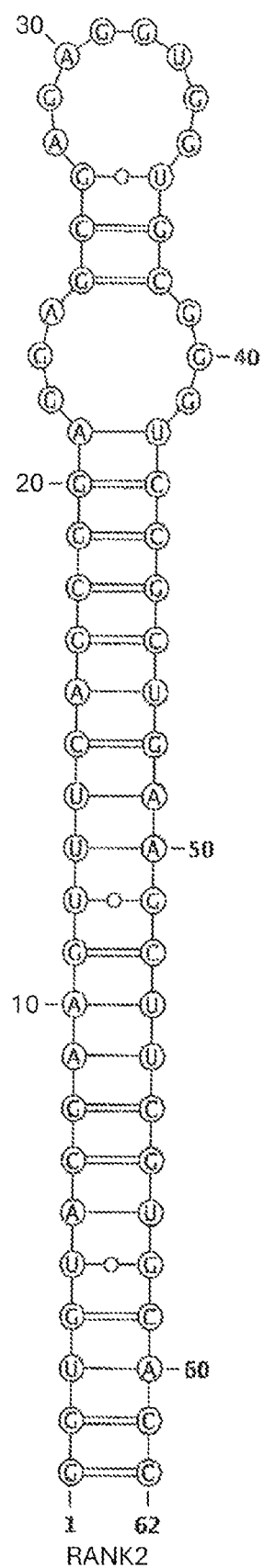
Figure 9:
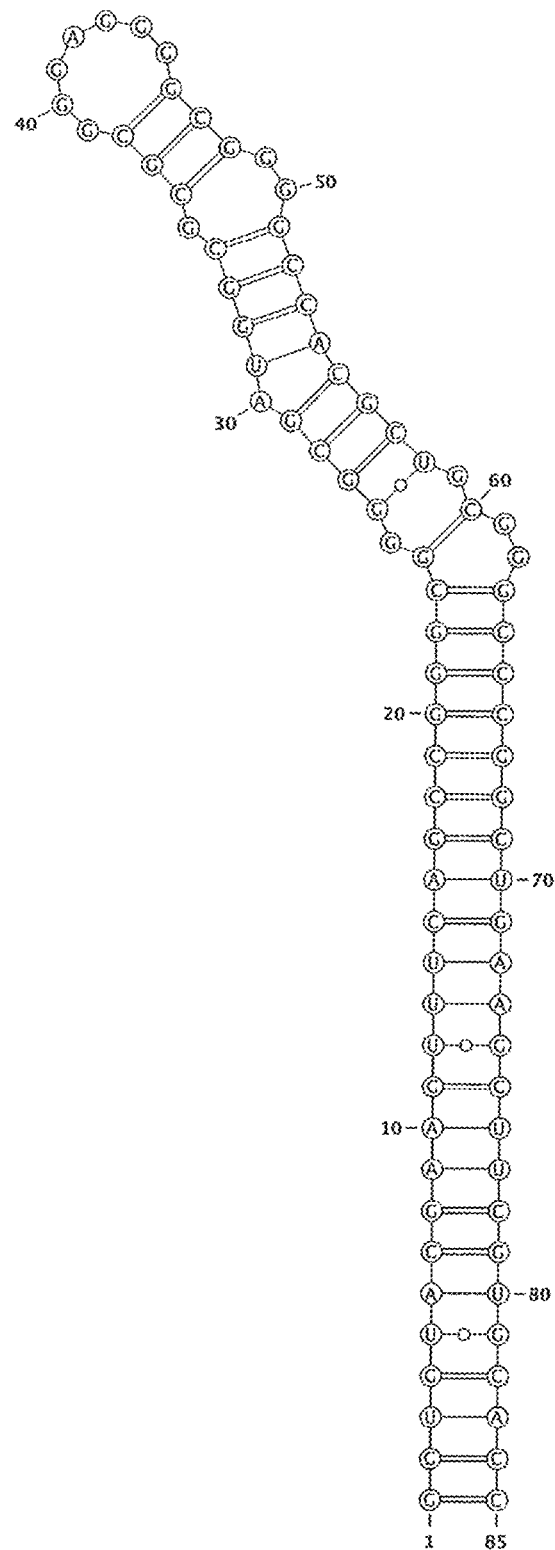
Figure 9:
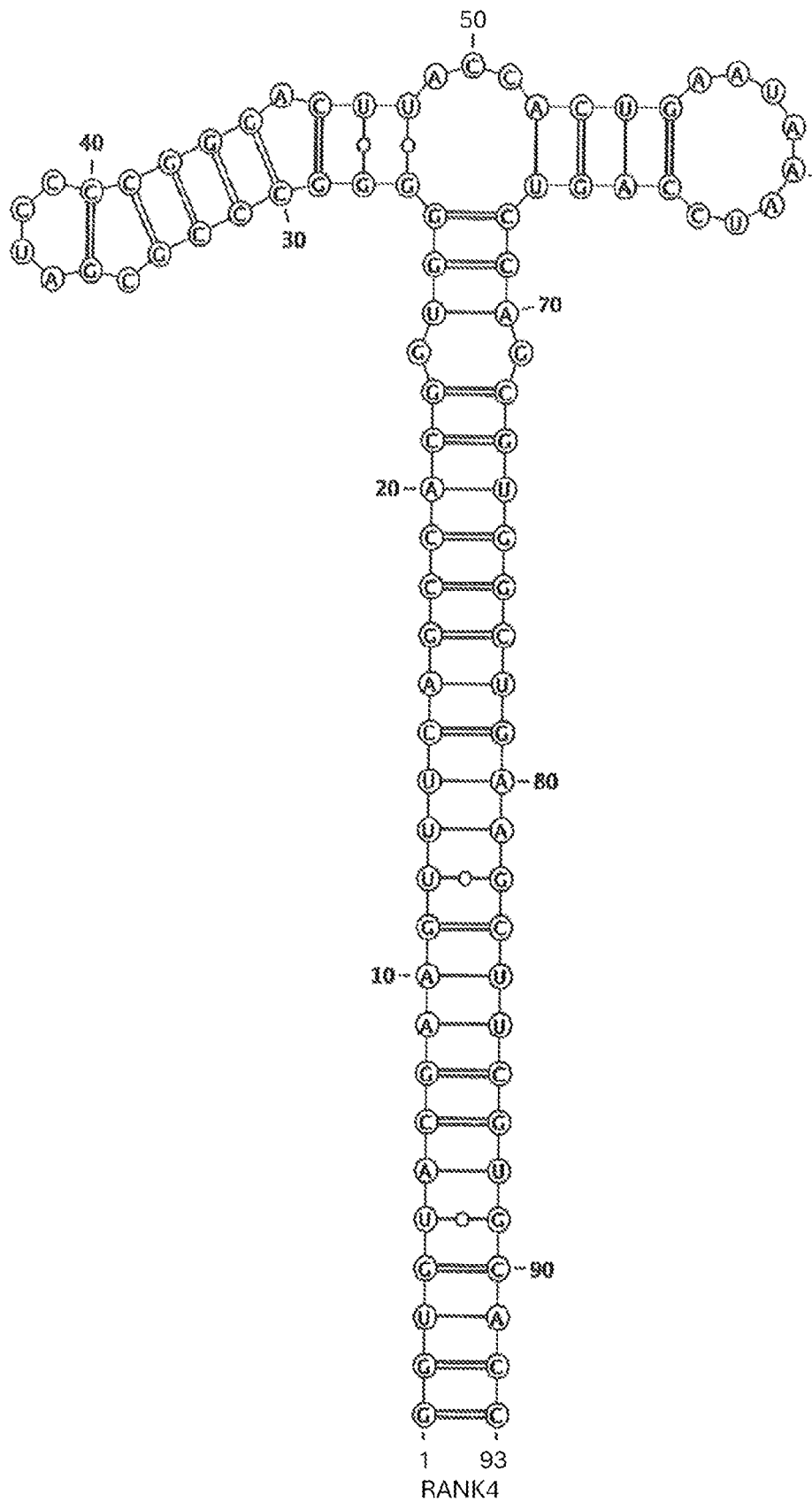
Figure 9:
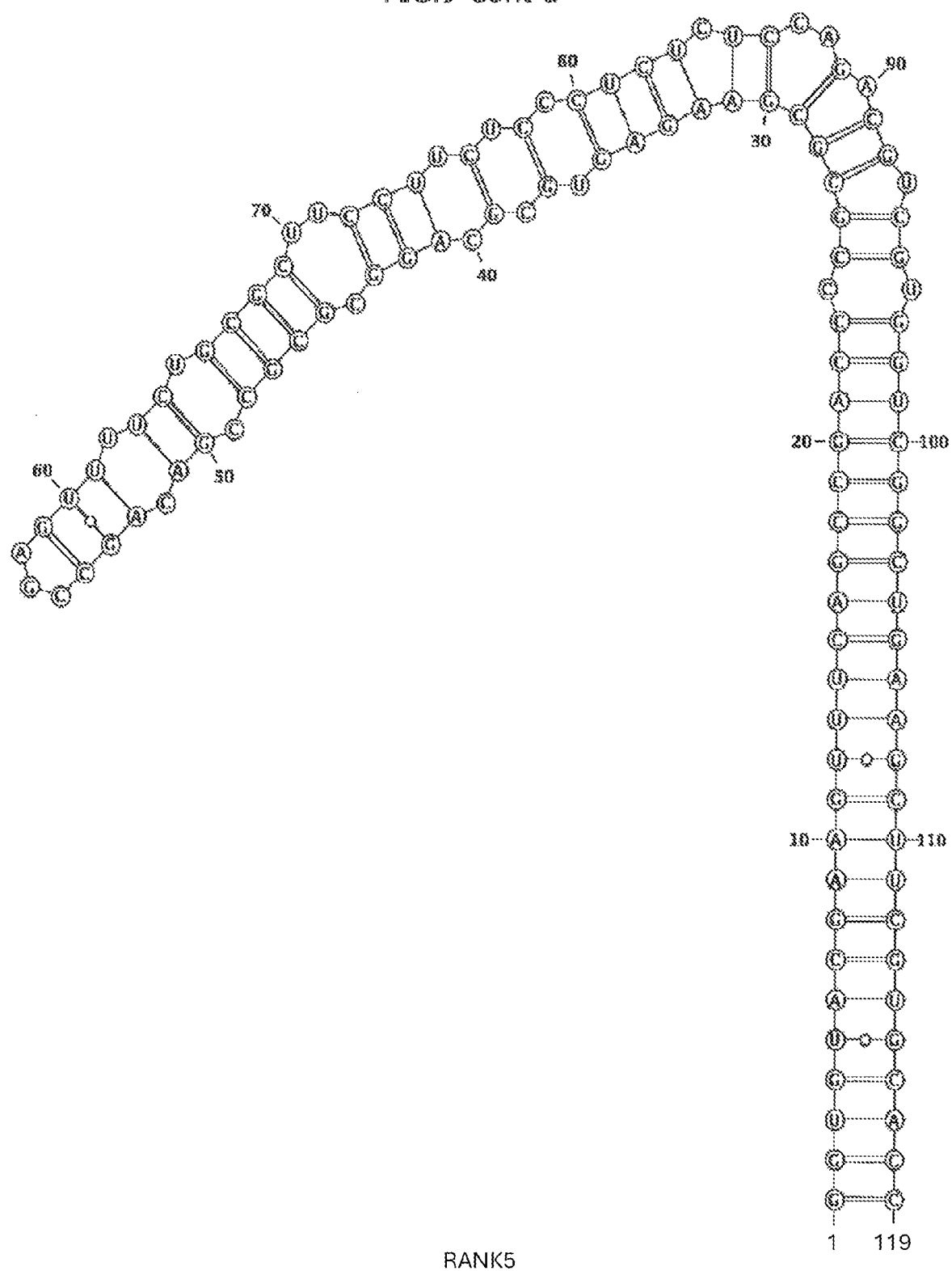
Figure 9:
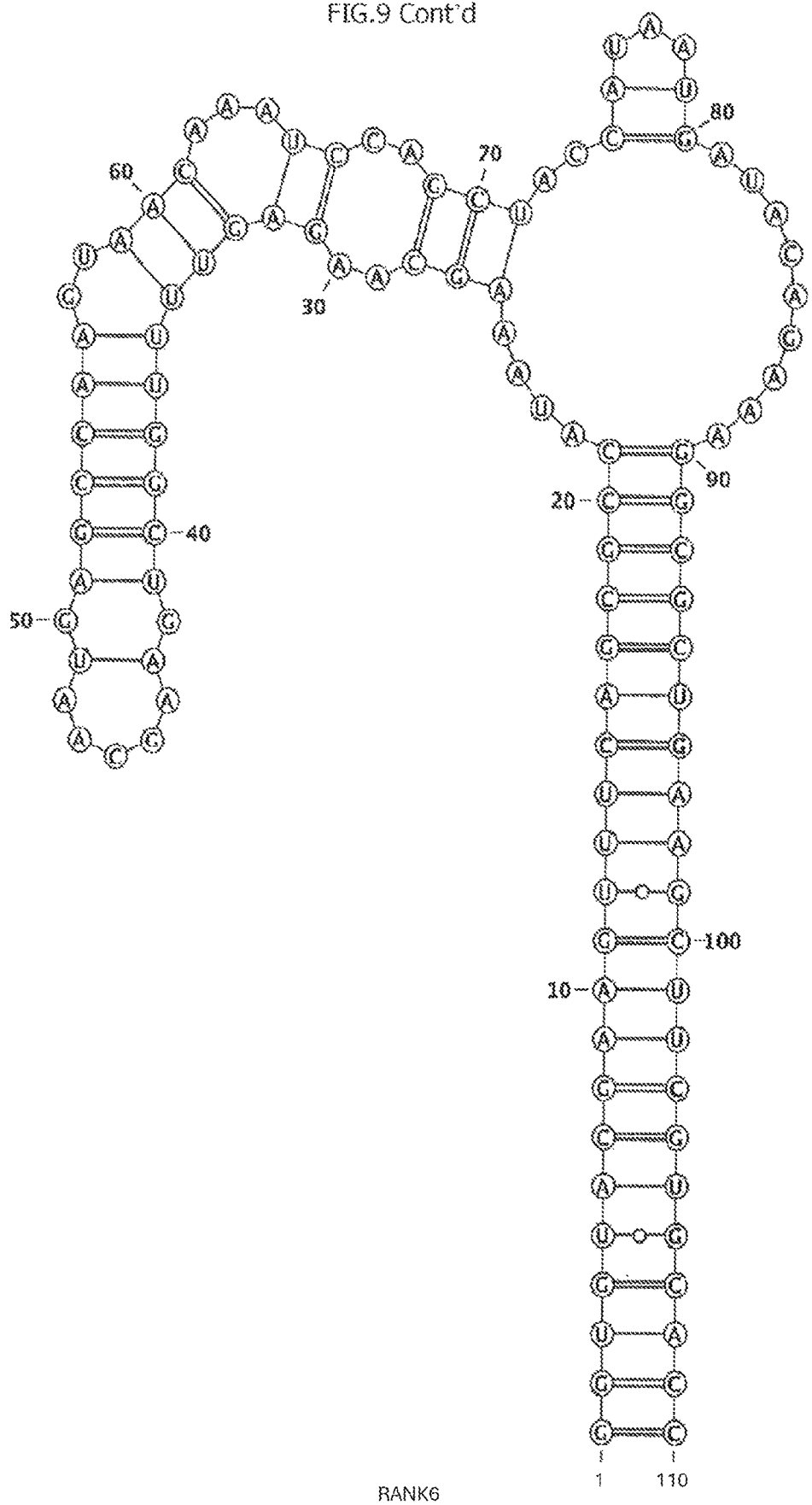
Figure 9:
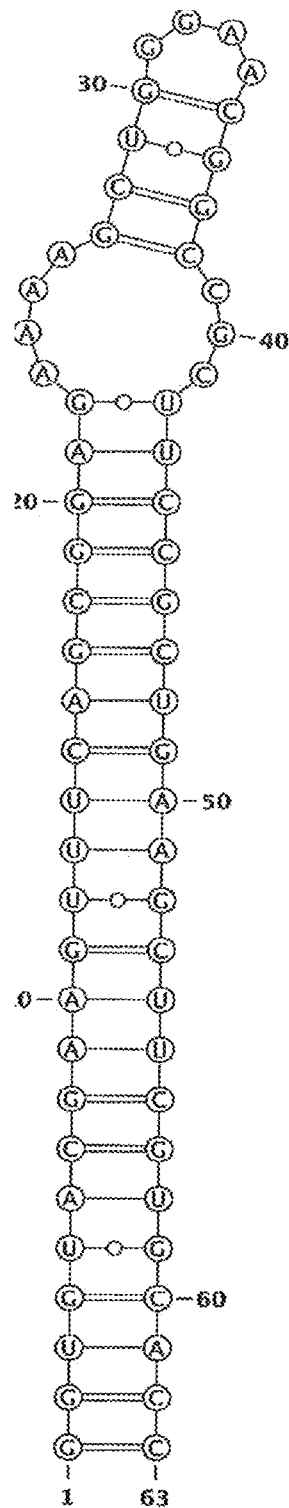
Figure 9:
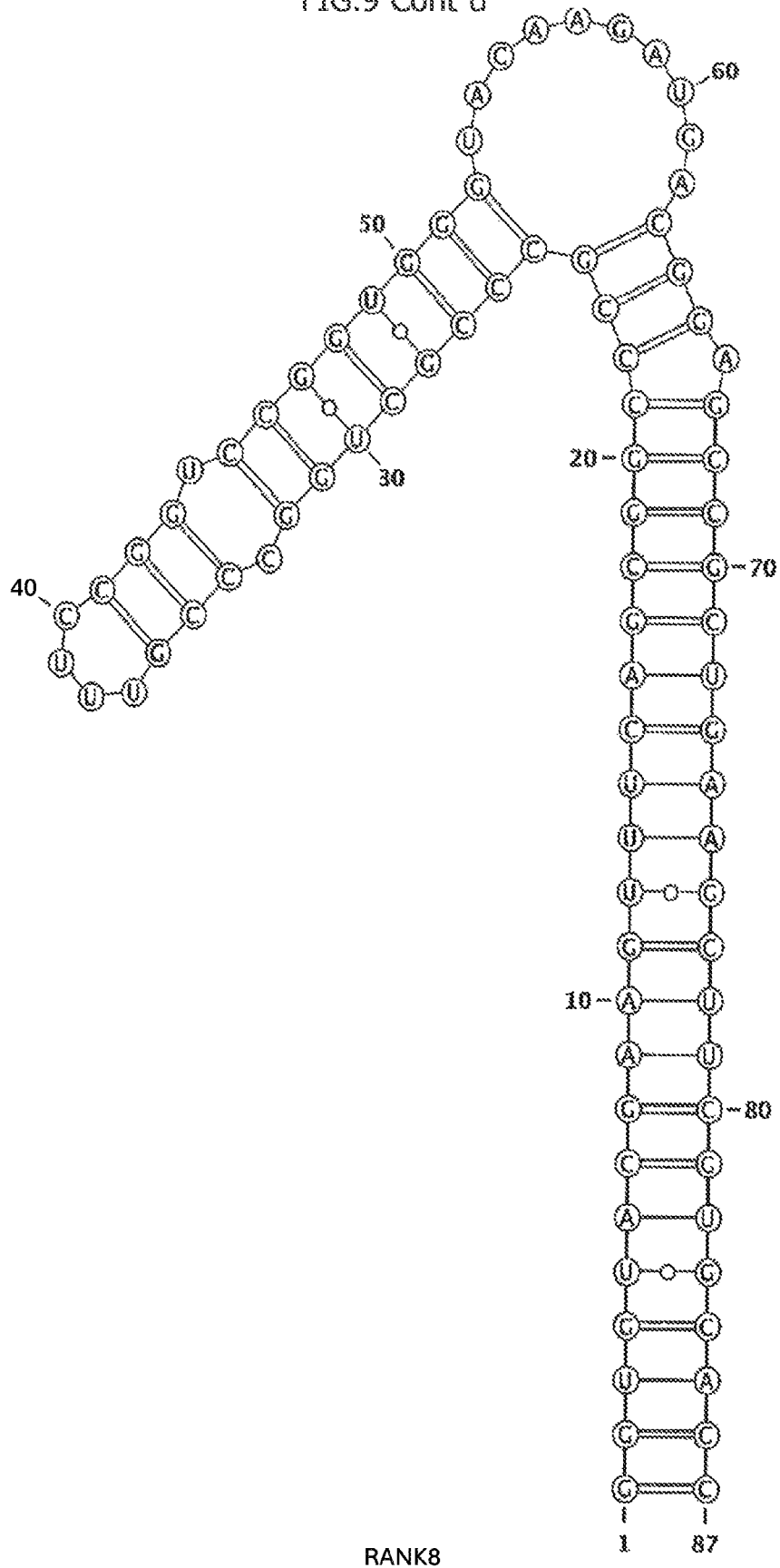
Figure 9:
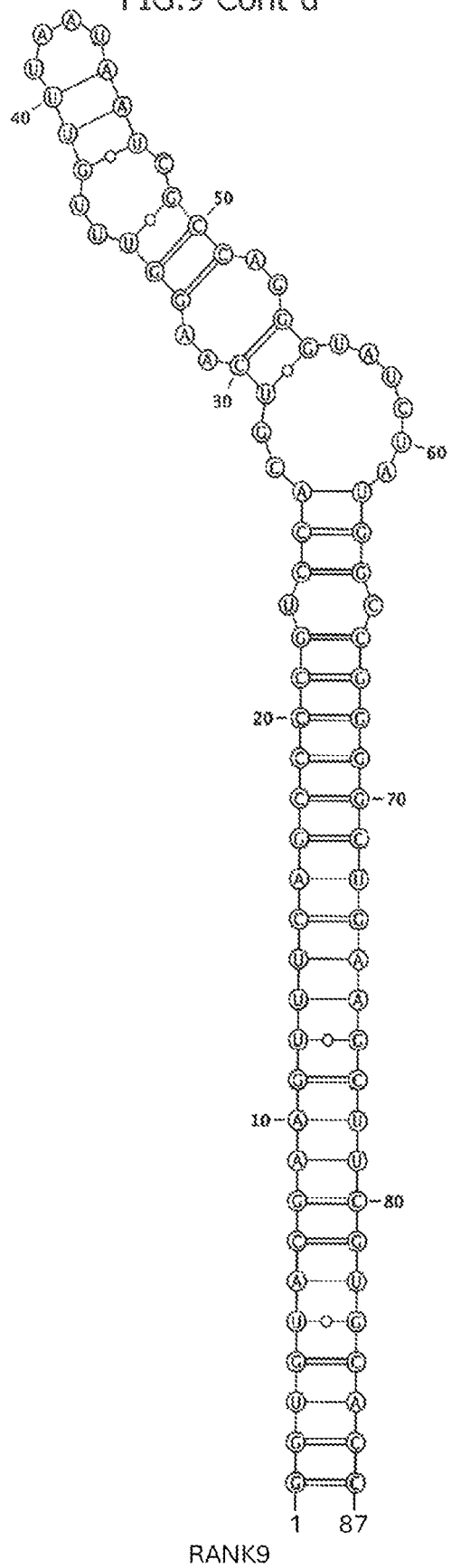
Figure 9:
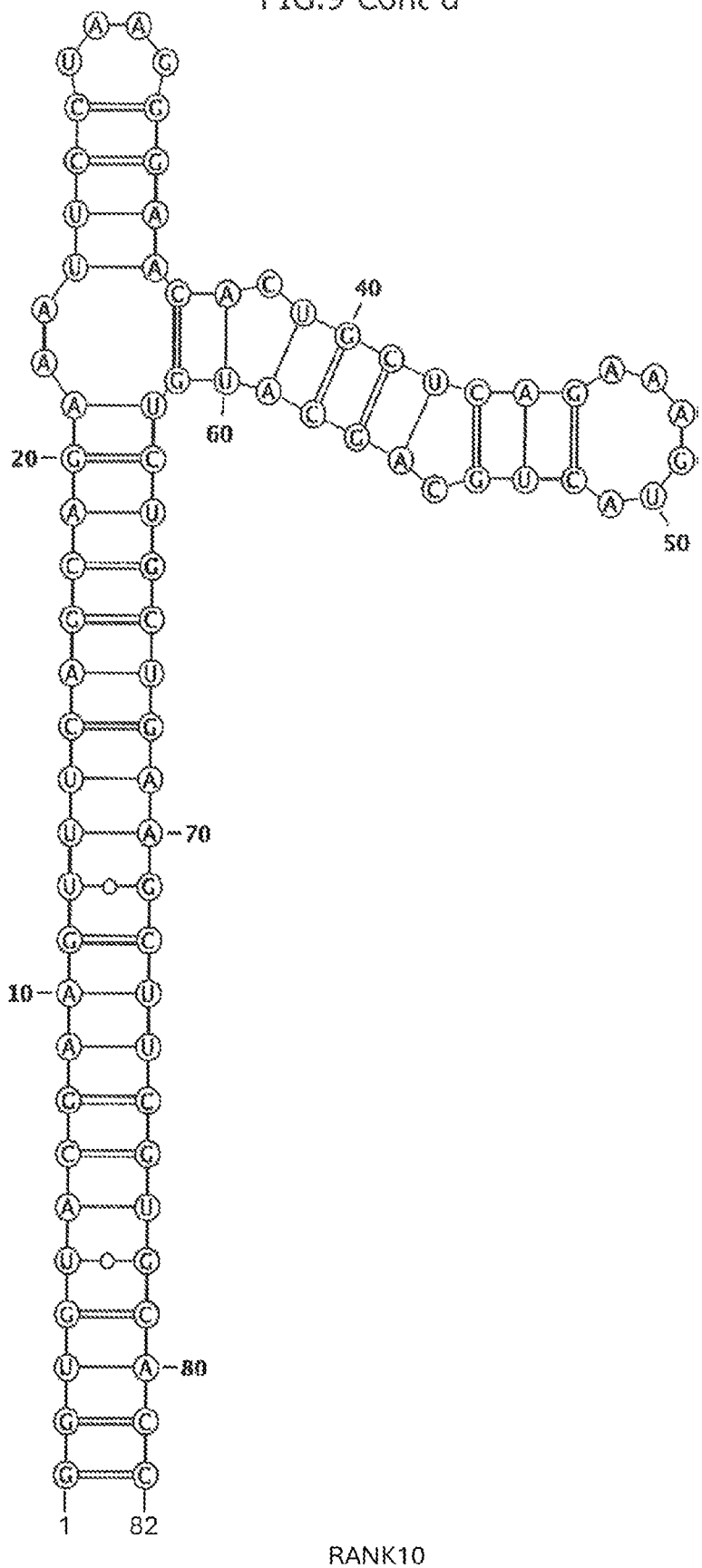
Figure 9:
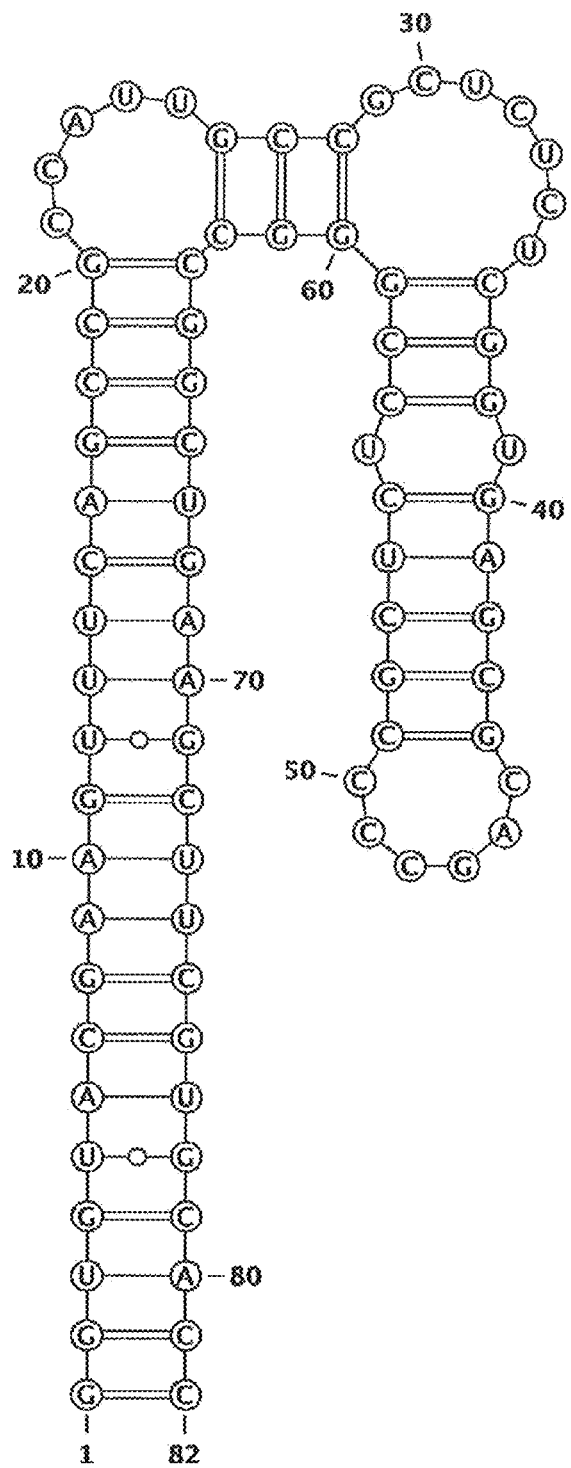
Figure 9:
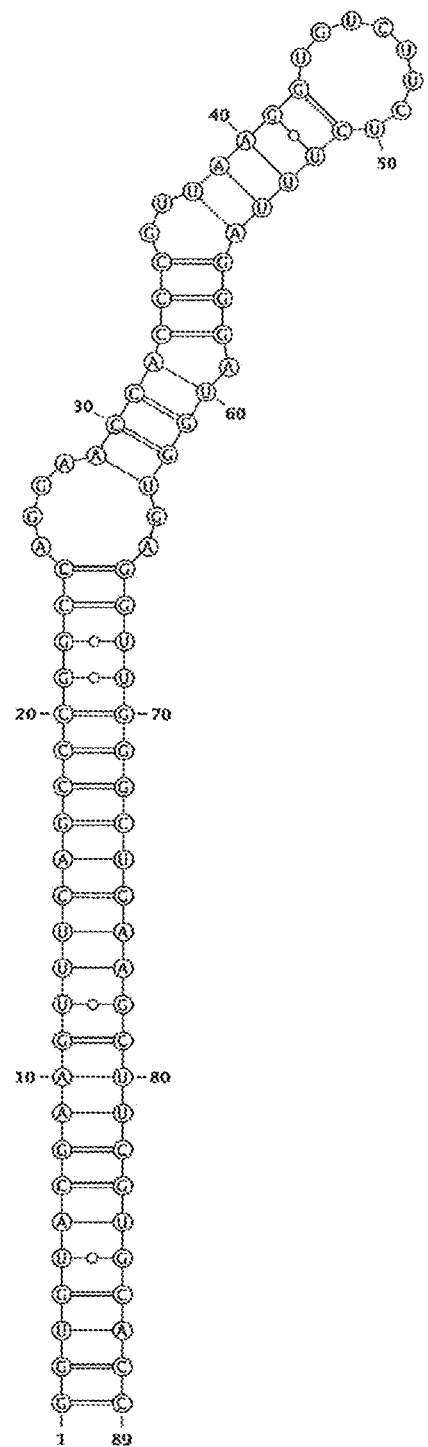
Figure 9:
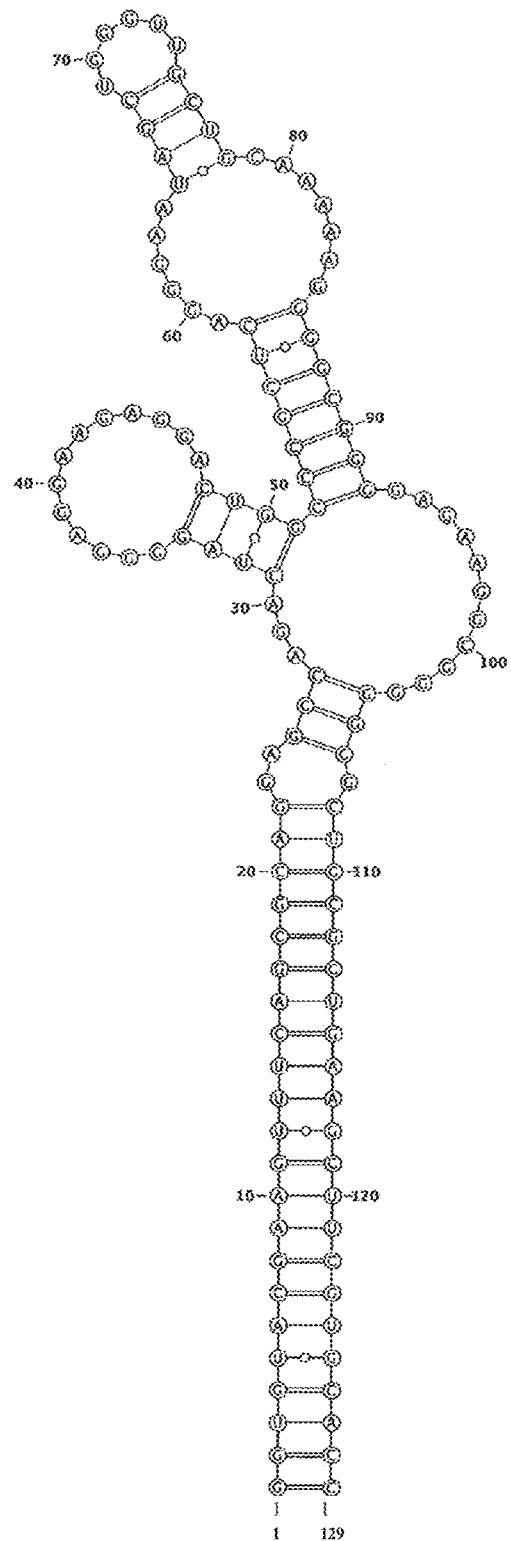
Figure 9:
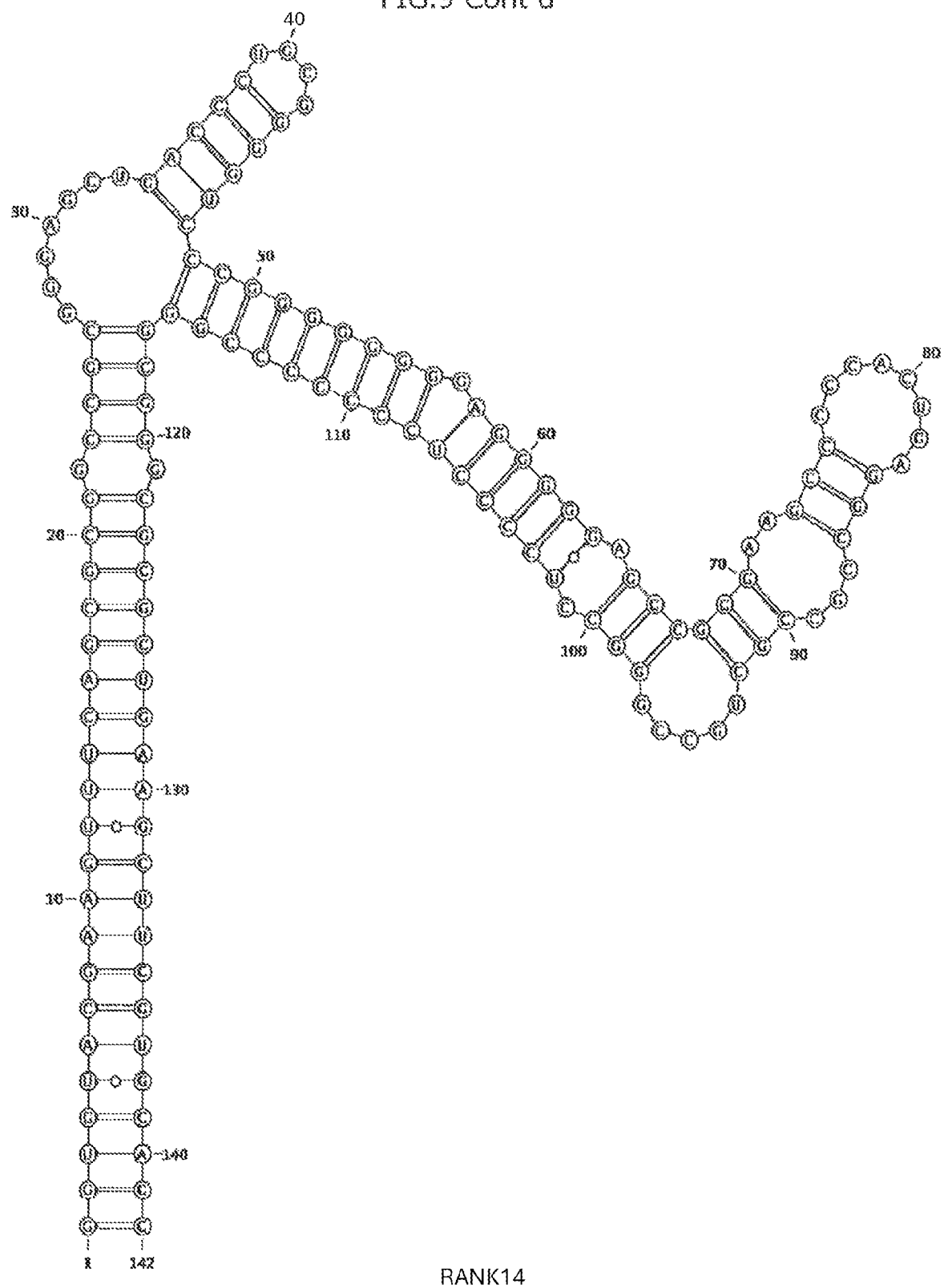
Figure 9:
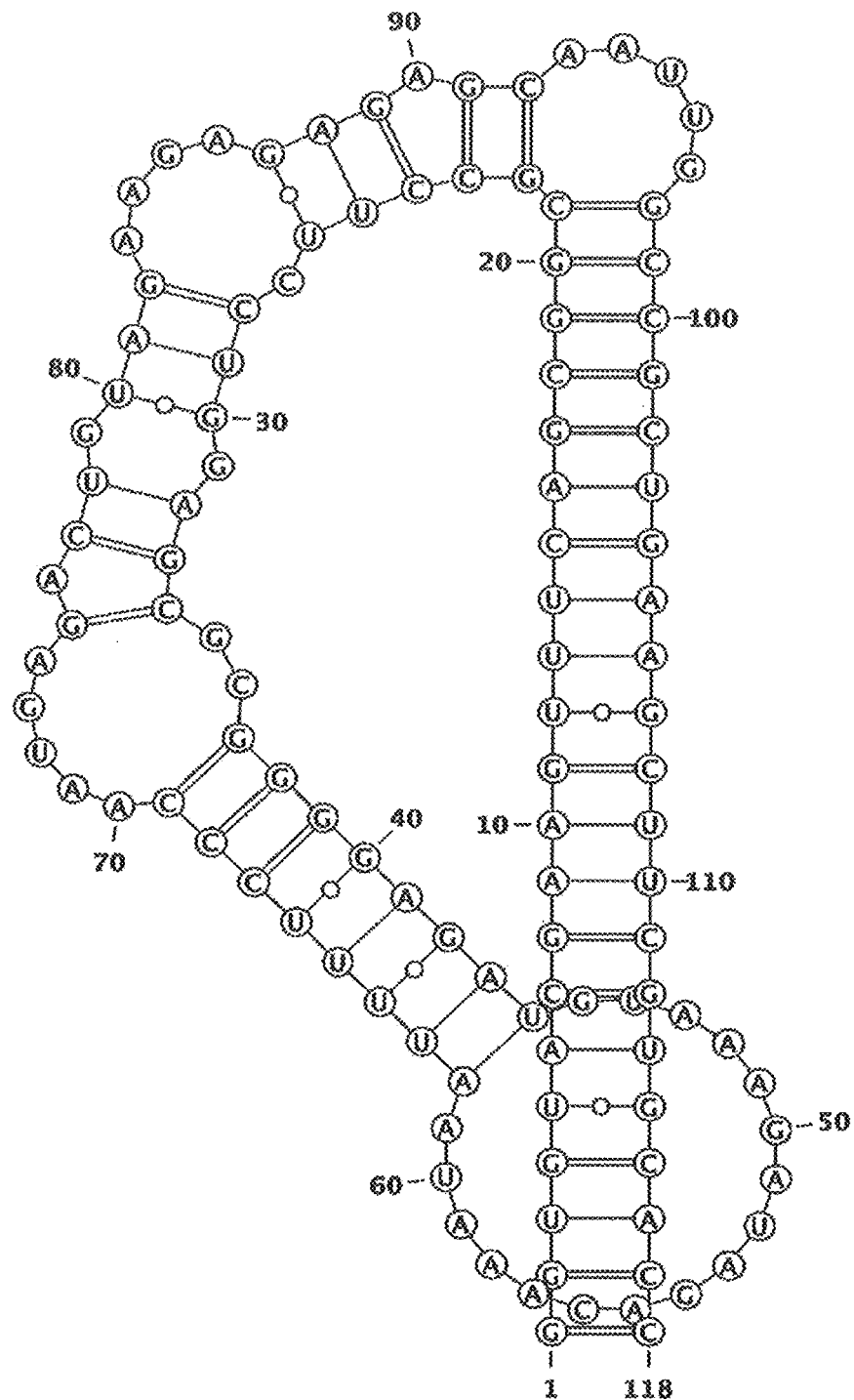
Figure 9:
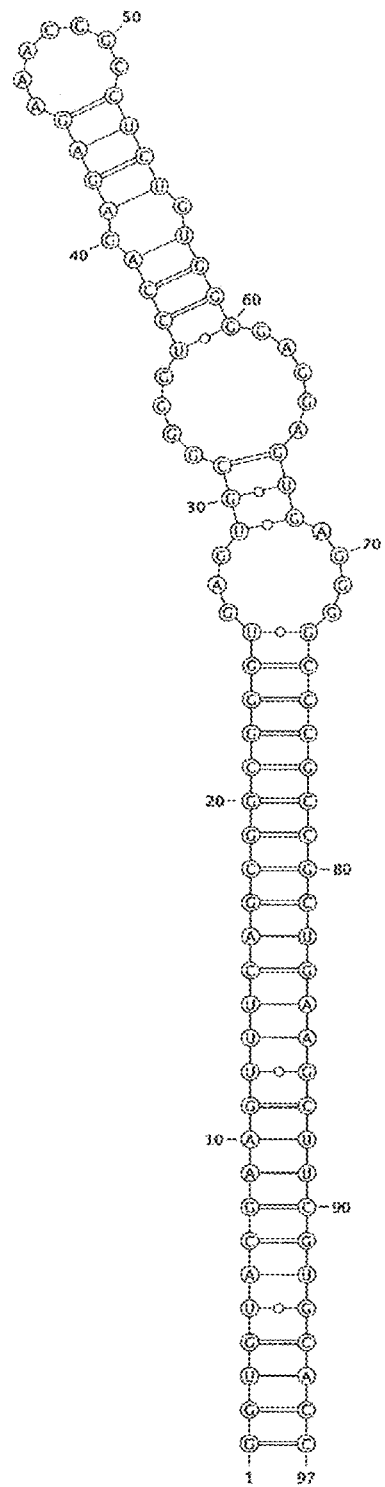
Figure 10:
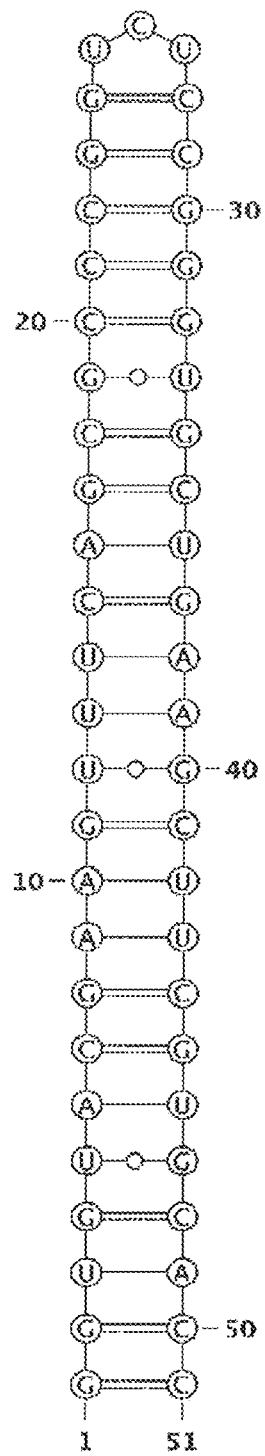
FIG. 10 is a diagram showing the secondary structures of RNAs ranked lower in ranking of the binding affinity to eIF3 complex.
Figure 10:
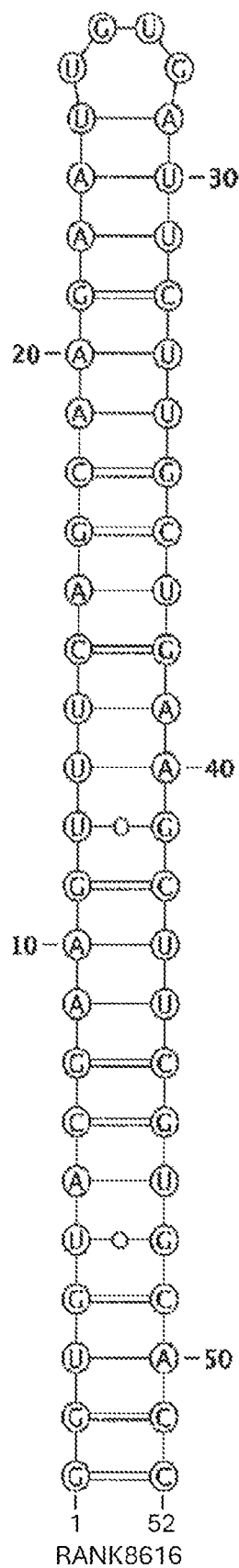
Figure 10:
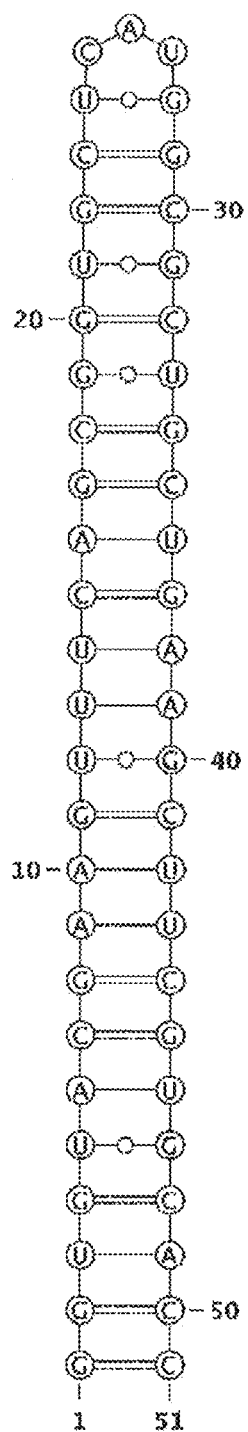
Figure 10:
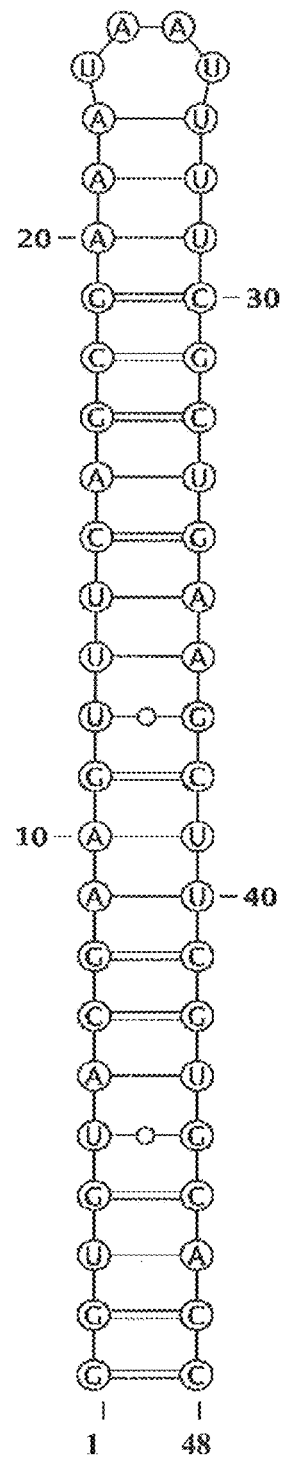
Figure 10:
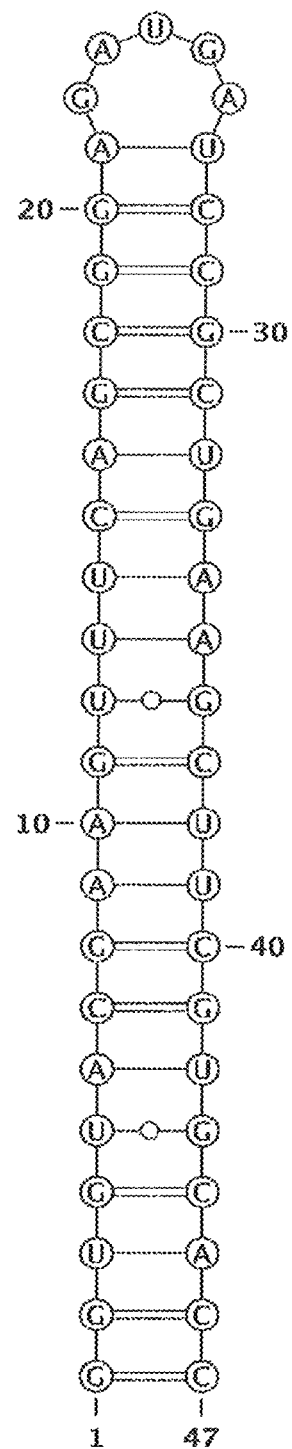
Figure 10:
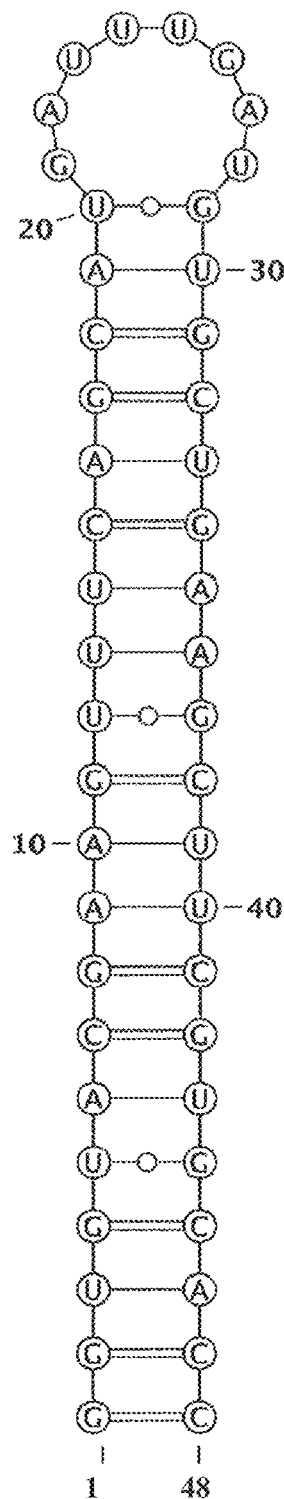
Figure 10:
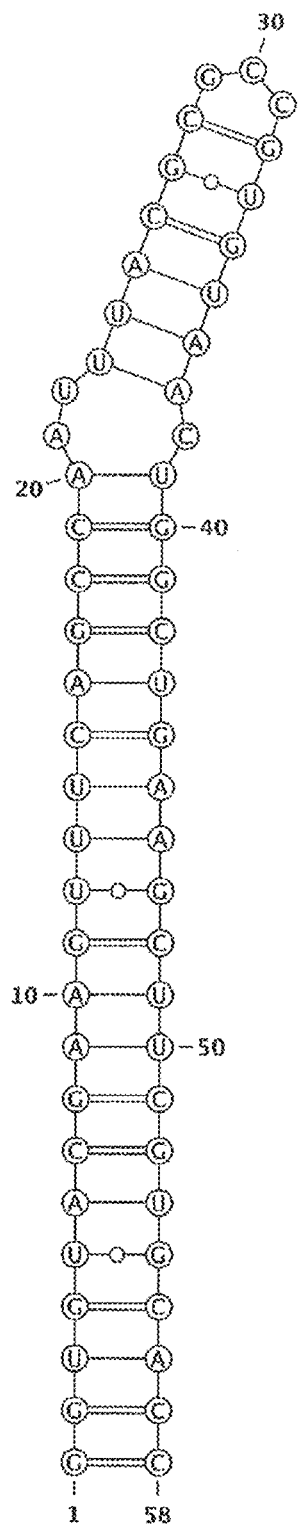
Figure 10:
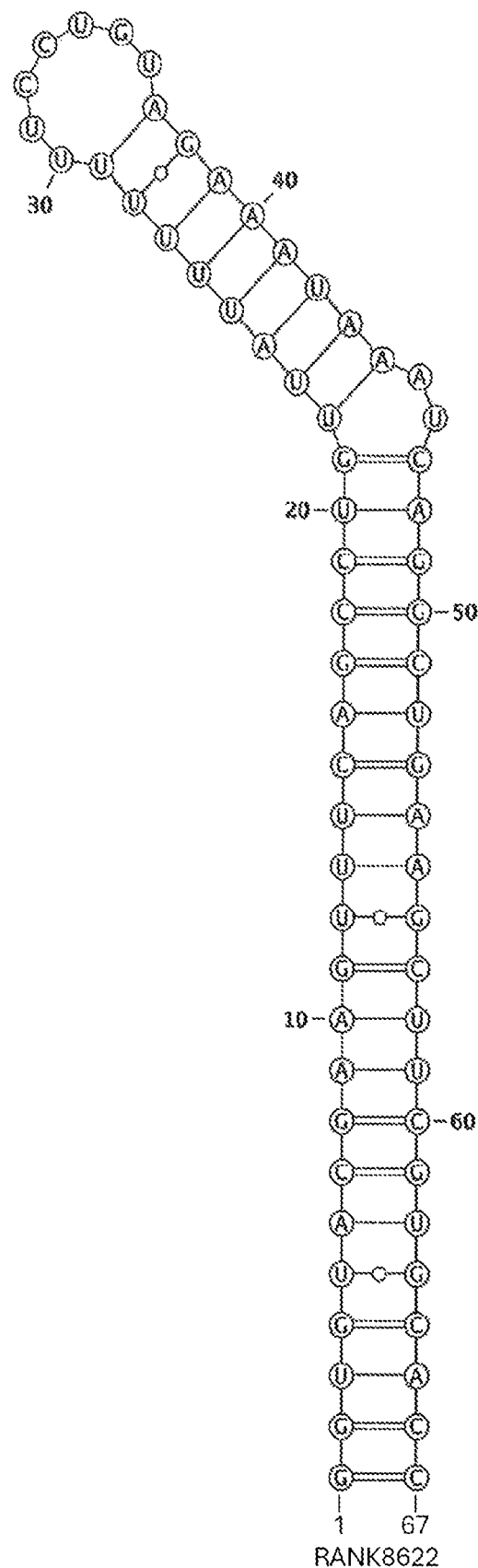
Figure 10:
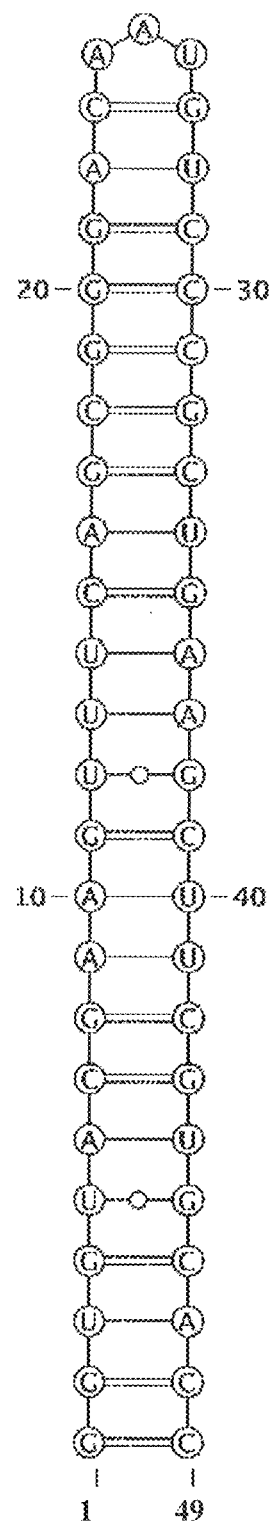
Figure 10:
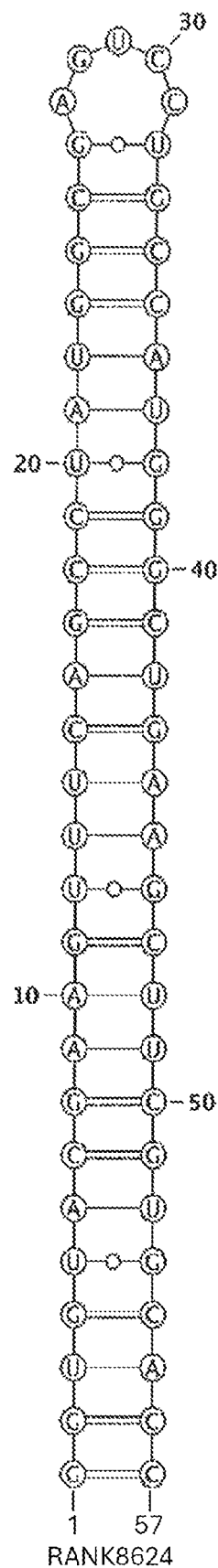
Figure 10:
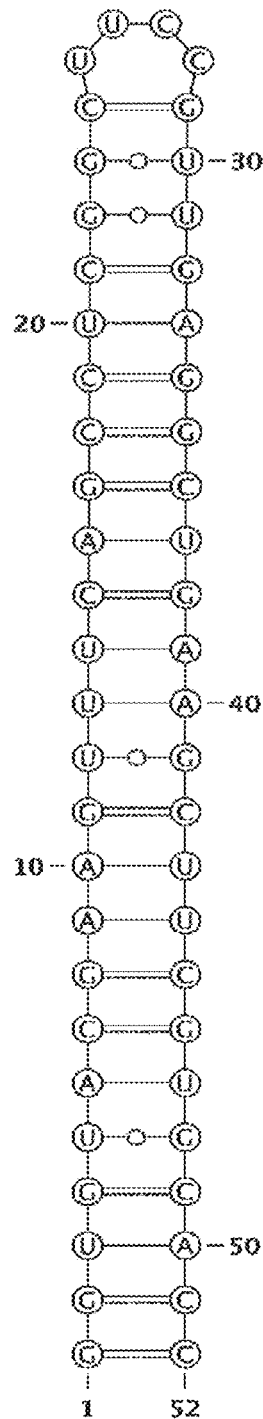
Figure 10:
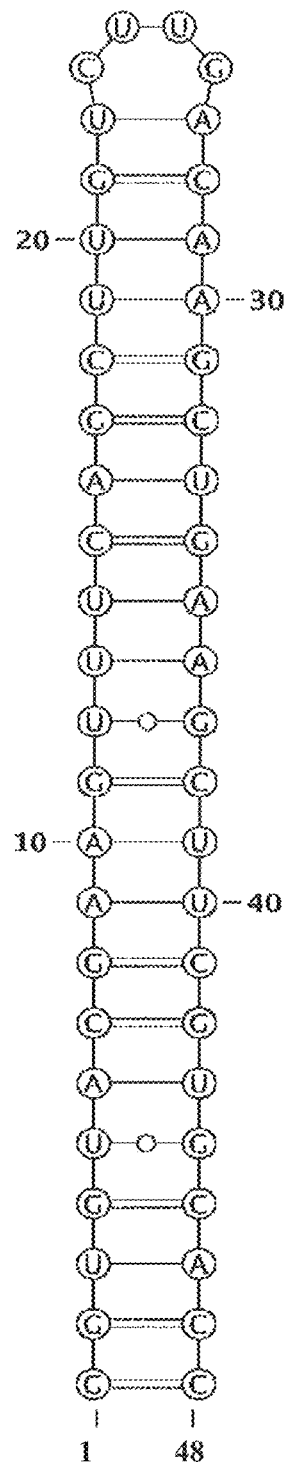
Figure 10:
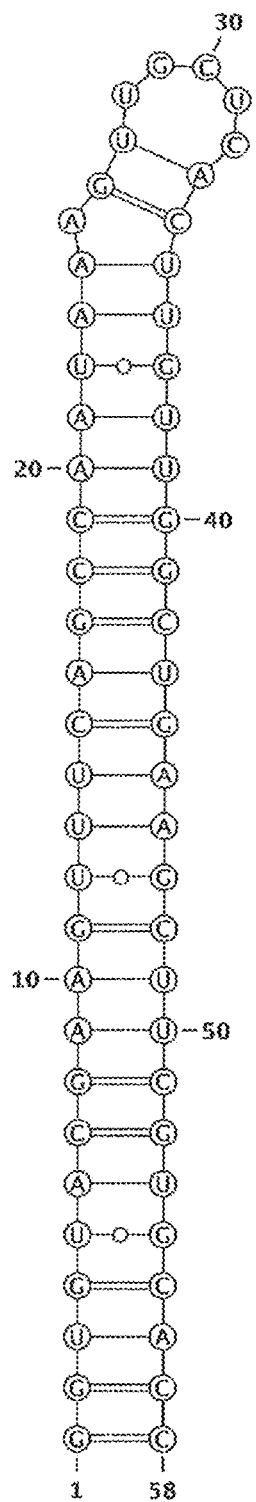
Figure 10:
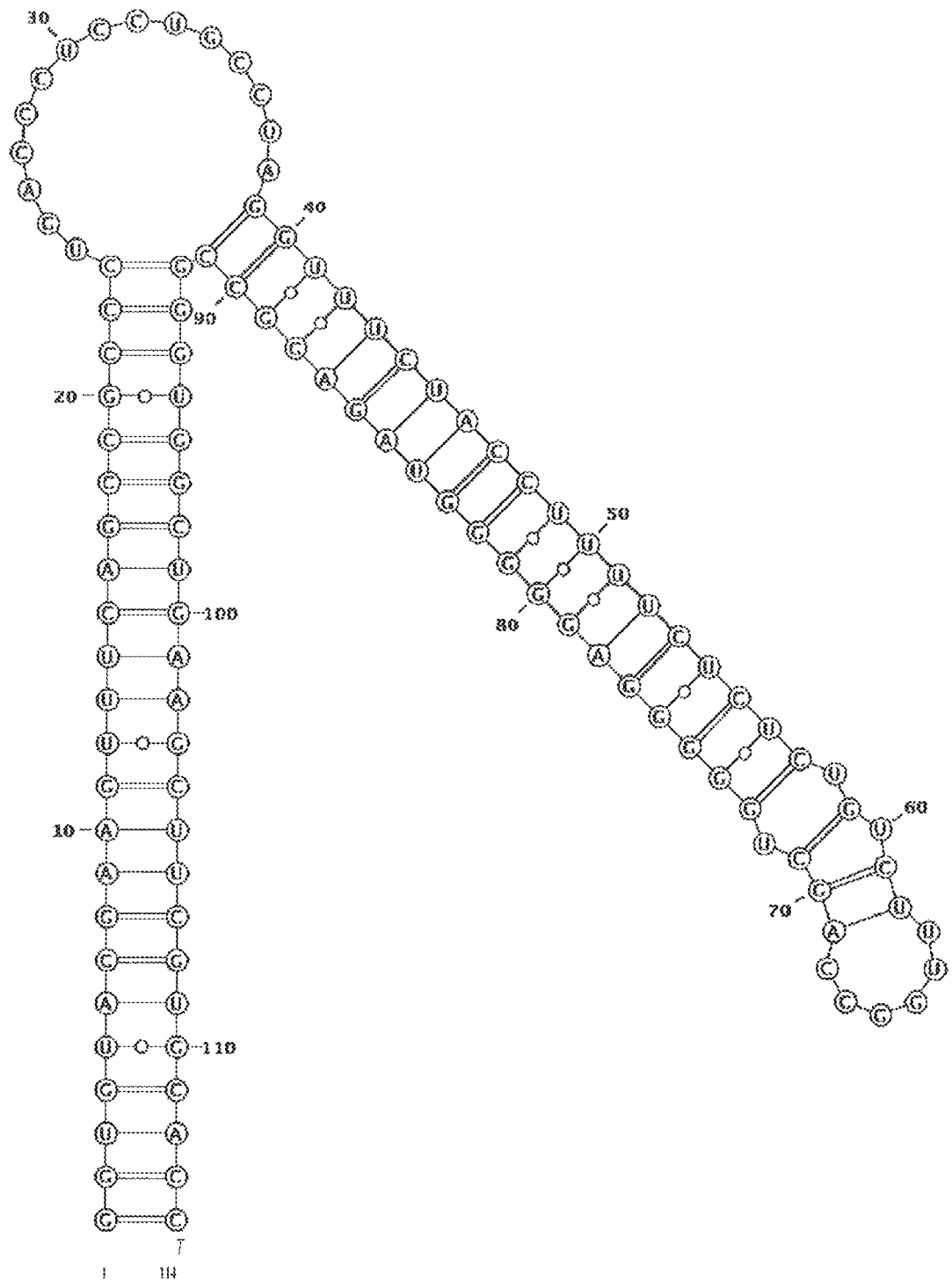
Figure 10:
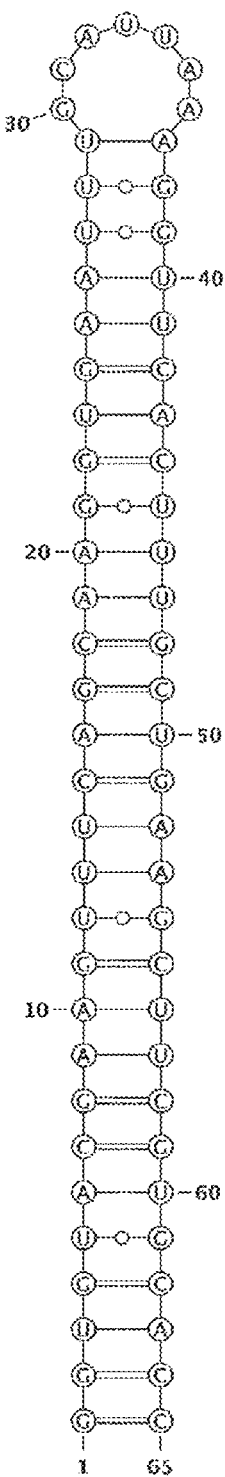
Figure 10:
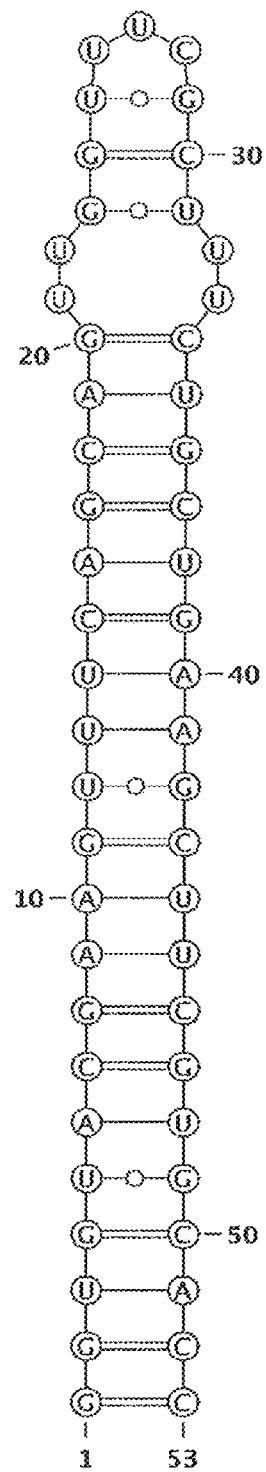

RNA structures were depicted for RNA sequences ranked higher (ranks 1 to 16) and RNA ranked lower (ranks 8615 to 8630) in ranking of the binding affinity to eIF3 complex. The results are shown in FIG. 9 and FIG. 10. Any RNAs ranked higher were long and formed robust secondary structures (FIG. 9). In contrast, many of the RNAs ranked lower were short and had a monotonous hairpin loop structure, while some of them were long but had a low binding affinity (FIG. 10). From these results, it was understood that the binding affinity depended on sequence motifs in RNAs and other structural features.

3-6. Detection of eIF3b-Binding RNA Structural Motifs in HIV-1 Genome

Among the results of scanning with a microarray, the top results of the eIF3b-binding RNA structural motifs related to the HIV-1 genome are shown in Table 2. The RNA structures contained in the HIV-1 gag IRES (Internal Ribosome Entry Site) region existing upstream of the 5' end of the HIV-1 genome were detected as having high binding affinities (rank 17 (top 0.2%) and rank 568 (top 6.6%)). These results showed that this method enables screening of functional RNA structural motifs regulating translation initiation such as IRES.

Table 2. eIF3b-binding RNA structural motifs and their region in the HIV-1 genome

TABLE 2

| Rank | Top (%) | Name | HIV-1 Genome Region |
|---|---|---|---|
| 6 | 0.07 | HIV_2014_Siegfried_nucs_1395_1714_1 | |
| 17 | 0.20 | HIV_2014_Siegfried_nucs_1_753_9 | HIV-1 gag IRES |
| 252 | 2.92 | HIV_2014_Siegfried_nucs_1395_1714_2 | |
| 468 | 5.42 | HIV_2014_Siegfried_nucs_1_753_1_Multi | 5'TAR |
| 568 | 6.58 | HIV_2014_Siegfried_nucs_1_753_2_Multi | HIV-1 gag IRES |
| 1071 | 12.41 | HIV_2014_Siegfried_nucs_8807_8914_1 | |
| 1088 | 12.61 | HIV_2014_Siegfried_nucs_1177_1351_4 | |
| 1115 | 12.92 | HIV_2014_Siegfried_nucs_8501_8785_Multi | PPT |
| 1163 | 13.48 | HIV_2014_Siegfried_nucs_1395_1714_2_Multi | |
| 1346 | 15.60 | HIV_2014_Siegfried_nucs_1177_1351_Multi | |
| 1684 | 19.51 | HIV_2014_Siegfried_nucs_7244_7603_Multi | RRE |
| 1763 | 20.43 | HIV_2014_Siegfried_nucs_4678_4773_2 | Part of 3'TAR |
| 1804 | 20.90 | HIV_2014_Siegfried_nucs_8982_9173_4 | |
| 2258 | 26.16 | HIV_2014_Siegfried_nucs_5449_6017_3 | |

Example 4. Confirmation of Practicality of Screening System for Functional RNA Structural Motifs (1)

In order to evaluate the reproducibility of the above screening method, two reproducibility experiments was performed independently from each other according to a procedure similar to that in Example 3, and correlation analysis was performed on the results.

Dynabeads-antibody-eIF3 complex was prepared according to the procedures similar to those in 3-1 and 3-2 above except that 25 µL of Dynabeads, 10 µL of anti-eIF3b antibody and HEK293FT cell lysate (1100 µg/µL) were used. Furthermore, eIF3b-binding RNA was purified according to the procedure similar to that in 3-3. According to the procedure similar to that in 1-1-E above, the purified RNA was dissolved in 18 µL of ultrapure water and subjected to scanning with a microarray to obtain fluorescence intensity data, and the data was analyzed.

For the evaluation of the binding affinity, the above data was normalized by the fluorescence intensity obtained for samples prepared using Dynabeads Protein A having no antibody bound thereto. The correlation coefficient was calculated from the results of two independent reproducibility experiments. The binding affinity and coefficient of variation (CV) for each RNA structure were calculated by using the mean and standard deviation for three RNA structure probes. RNA structure in which the value of the variation coefficient was 1 or more was excluded from the analysis.

Figure 11:
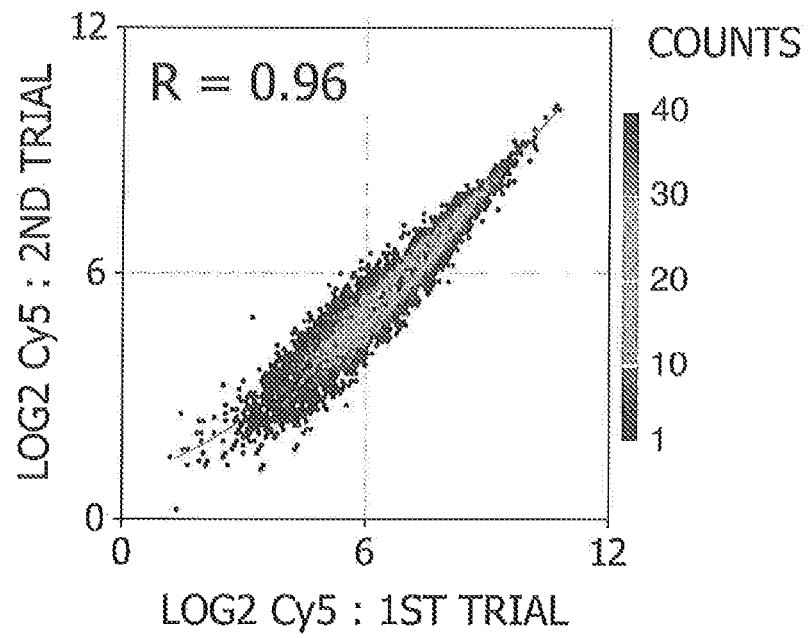
FIG. 11 is a scatter plot of the fluorescence intensities each of which corresponds to each of RNA structures detected by two independent screenings.
Figure 12:
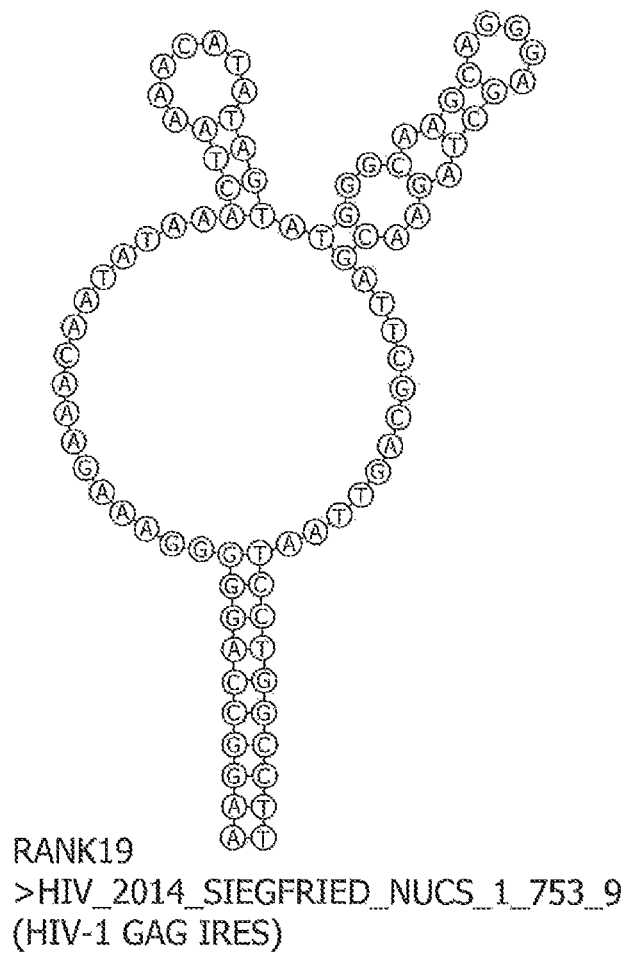
FIG. 12 is a diagram showing the structure of HIV-1 gag IRES.

The results are shown in FIG. 11. The horizontal axis shows the fluorescence intensity corresponding to each RNA structure obtained by the first round of reproducibility experiments, and the vertical axis shows the fluorescence intensity corresponding to each RNA structure obtained by the second reproducibility experiment. The scale value shows the frequency. As shown in FIG. 11, it was possible to obtain RNA structures with high reproducibility with a correlation coefficient (r)=0.96. Moreover, this reproducibility experiment made it possible to detect again HIV-1 gag IRES, which was known to strongly bind to the eIF3-40S ribosomal subunit complex and was detected in 3-6 above (FIG. 12). From these results, it was confirmed that this experimental system is sufficiently practical as a screening method.

Example 5. Confirmation of Practicality of Screening System for Functional RNA Structural Motifs (2)

A pull-down assay was performed on RNAs, ranked higher in ranking of the binding affinity to eIF3 complex, by the above screening method, and the binding affinities of RNAs were compared with each other according to the following procedure.

5-1. Preparation of DNA/RNA Probes for Pull-Down Assay

A. Preparation of RNA Probes

An assistive sequence was added to each of the RNAs ranked higher in ranking of the binding affinity to eIF3 complex to prepare an RNA probe. The RNA probe was prepared by in vitro transcription of a template DNA according to the procedure similar to that in 1-1-B above. The template DNA used was a DNA comprising a sequence obtained by converting, to reverse complementary strands, a sequence composed of, from the 5' end in order, (i) T7 promoter+G, (ii) barcode sequences (25 bases), (iii) Stem forward sequence, (iv) an RNA structure sequence and (v) Stem reverse sequence.

TABLE 3

Sequences of template DNAs to RNA probes

| ID | DNA sequence | SEQ ID NO: |
|---|---|---|
| Rank1_Pulldown_RNA_Probe_template | GGTGCACGAGGGACCCGCACCACCTCTCGCTCCTCCCTCGTACACCCCAGACTCACAGCCGCGCTAGTATCCTATAGTGAGTCGTATTAGC | 10 |
| Rank8531_Pulldown_RNA_Probe_template | GGTGCACGAGCAGGTTAGTCCAAACACCTGCTCGTACACCCCAGACTCACAGCCGCGCTAGTATCCTATAGTGAGTCGTATTAGC | 11 |
| Rank5_Pulldown_RNA_Probe_template | GGTGCACGAGCGGGCCCGCAGCGTGGCCCCGCCCCTCCCGCGCGCCATCGCCCCGCCCGCTCGTACACCCCAGACTCACAGCCGCGCTAGTATCCTATAGTGAGTCGTATTACC | 12 |
| Rank10_Pulldown_RNA_Probe_template | GGTGCACGAGGGCCTTTCTGTATCATTATGGTAGCTGGATTTGTTACTTGGCTCATTGCTTCAGCCAAAACTCTTGCTTTATGGCCTCGTACACCCCAGACTCACAGCCGCGCTAGTATCCTATAGTGAGTCGTATTAGC | 13 |
| Rank19(PC, ~4stem)_Pulldown_RNA_Probe_template | GGTGCACGAGGGCCAGGATTAACTGCGAATCGTTCTAGCTCCCTGCTTGCCCATACTATATGTTTTAGTTTATATTGTTTCTTTCCCCCTGGCCCTCGTACCCCAGACTCACAGCCGCGCTAGTATCCTATAGTGAGTCGTATTAGC | 14 |

TABLE 4

Sequences of RNA probes

| ID | RNA sequence | SEQ ID NO: |
|---|---|---|
| Rank1_Pulldown_RNA_Probe | GGAUACUAGCGCGGCUGUGAGUCUGGGGUGUACGAGGGAGGAGCGAGAGGUGGUGCGGGUCCCUCUCGUGCACC | 15 |
| Rank8531_Pulldown_RNA_Probe | GGAUACUAGCGCGGCUGUGAGUCUGGGGUGUACGAGCAGGUGUUUGGACUAACCUGCUCGUGCACC | 16 |
| Rank5_Pulldown_RNA_Probe | GGAUACUAGCGCGGCUGUGAGUCUGGGGUGUACGAGCGGGCGGGGCGAUGGCGCGCGGGAGGGGCGGGGCCACGCUGCGGGCCCGCUGGUGCACC | 17 |
| Rank10_Pulldown_RNA_Probe | GGAUACUAGCGCGGCUGUGAGUCUGGGGUGUACGAGGCCAUAAAGCAAGAGUUUUGGCUGAAGCAAUGAGCCAAGUAACAAAUCCAGCUACCAUAAUGAUACAGAAAGGCCCUCGUGCACC | 18 |
| Rank19(PC, -4stem)_Pulldown_RNA_Probe | GGAUACUAGCGCGGCUGUGAGUCUGGGGUGUACGAGGGCCAGGGGAAAGAAACAAUAUAAACUAAAACAUAUAGUAUGGGCAAGCAGGGAGCUAGAACGAUUCGCAGUUAAUCCUGGCCCUCGUGCACC | 19 |

B. Preparation of Biotinylated DNA Barcode Probes

Biotinylated DNA barcode probes for immobilizing the RNA probes on magnetic beads were prepared. Each of the biotinylated DNA barcode probes was designed so as to comprise, from the 5' end in order, (i) a complementary sequence to the barcode sequence (25 bases), (ii) C (1 base), (iii) a spacer (3 bases) and (iv) 3' end biotin modification. The biotinylated DNA barcode probes were synthesized by outsourcing to Fasmac (normal scale, HPLC purification).

3'-biotinylated DNA Probe Barcode 25 mer+C+3spacer (SEQ ID NO: 20)
CCAGACTCACAGCCGCGCTAGTATCCAAG-(Biotin)

C. Preparation of DNA/RNA Probe for Pull-Down Assay

2 µL of 5× Hybridization Buffer (100 mM HEPES pH 7.8, 400 mM KCl, 100 mM NaCl), 1 µL of a biotinylated DNA barcode probe (100 µM) and 120 pmol of an RNA probe were added in a 0.2 ml tube, and ultrapure water was added thereto to make up to 10 µL. The obtained probe liquid was subjected to heat treatment at 95° C. for 5 minutes in a thermal cycler, then cooled to 4° C. at −0.1° C./s and allowed to stand for 10 minutes to obtain a DNA/RNA probe for a pull-down assay.

5-2. Pull-Down Assay

The DNA/RNA probes for pull-down assays were immobilized on magnetic beads according to the following procedure. 50 µL of Streptavidin Mag Sepharose (GE Healthcare) was dispensed into 1.5 ml tubes. After placing each of the tubes in a magnetic rack to remove a supernatant, 500 μL of Binding Buffer (20 mM HEPES pH 7.8, 80 mM KCl, 20 mM NaCl, 10% glycerol, 2 mM DTT, 0.2 μg/μL BSA) was added thereto and mixed by inversion. After placing each of the tubes in the magnetic rack to remove a supernatant, 500 μL of Binding Buffer and 10 μL of the DNA/RNA probe for a pull-down assay prepared in 5-1 above were added thereto and the magnetic beads were stirred at 4° C. for 3 hours with a tube rotator. Subsequently, after placing each of the tubes in the magnetic rack to remove a supernatant, the magnetic beads were washed twice with 600 μL of Binding Buffer.

600 μL of Binding Buffer and 2 μL of RNase inhibitor Murine (NEB, 40 U/mL) were added to the obtained magnetic beads, and 200 μL of HEK293FT cell lysate (1100 μg/μL) was further added thereto. After stirring at 4° C. for 12 hours with the tube rotator, each of the tubes was placed in the magnetic rack to remove a supernatant. The magnetic beads were washed four times with 900 μL of Binding Buffer. Finally, 20 μL of 5× Sample Buffer 2 (ProteinSimple) was added to the magnetic beads, heated at 95° C. for 5 minutes and then left to stand at room temperature for 10 minutes. The magnetic beads were spun down and each of samples was collected.

Each of the collected samples was diluted five-fold with 0.1× Sample Buffer 2 (ProteinSimple), and then mixed with a 5× fluorescent master mix at a ratio of 1:4. Thereafter, the mixture was vortexed for 3 seconds and heated at 95° C. for 5 minutes. The eIF3 complex pulled down with DNA/RNA probe-magnetic beads was detected according to the standard protocol Wes (ProteinSimple) using a rabbit anti-eIF3b antibody (Bethyl) which had been diluted 1:20 with Antibody Diluent 2 (ProteinSimple).

Figure 13:
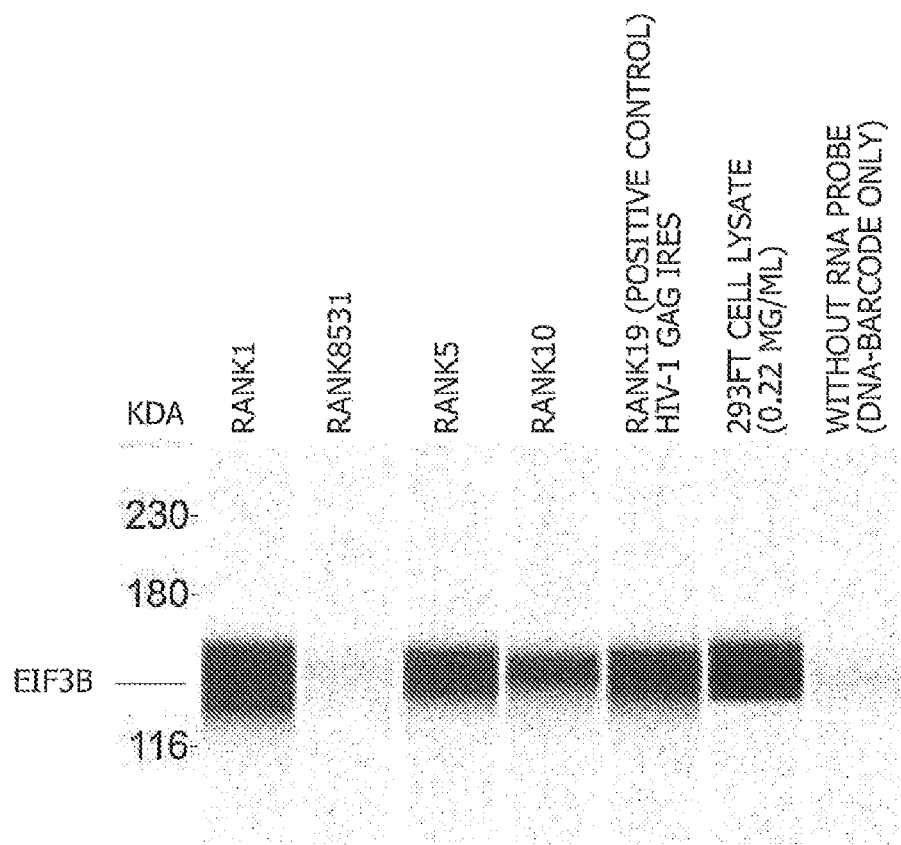
FIG. 13 is a diagram showing the results of a pull-down assay for confirming the binding affinities of RNAs ranked higher in the screening to the eIF3 complex.

The results are shown in FIG. 13. Any of the RNAs ranked higher in ranking of the binding affinity to eIF3 complex (Rank 1, Rank 5, Rank 10) exhibited the binding affinity similar to that of HIV-1 gag IRES (positive control). On the other hand, any of the RNAs ranked lower in ranking of the binding affinity to eIF3 complex did not exhibit the binding affinity to eIF3 complex. These results supported that the functional RNA structures could be accurately screened by the above screening method.

The invention claimed is:

1. A method for preparing an RNA probe, comprising the following steps:

(1) recognizing one or more stem structures contained in an RNA based on RNA sequence information, and selecting an RNA containing a plurality of stem-loop structures;

(2) extracting a plurality of RNA structures having a multi-branched loop from the RNA selected in the step (1), comprising the following steps (2a) to (2d):

(2a) selecting one stem-loop structure from the RNA selected in the step (1) and recording the stem-loop structure;

(2b) replacing the one stem-loop structure selected in the step (2a) with a single-stranded structure;

(2c) changing the selected stem-loop structure and repeating the steps (2a) and (2b) until the RNA is in a single single-stranded structure;

(2d) restoring the single single-stranded structure by all of the stem-loop structures recorded in the step (2a) or restoring a portion of the single single-stranded structure by one or more of the stem structures recorded in the step (2a);
(3) adding a first assistive stem portion sequence and a second assistive stem portion sequence to each of the extracted plurality of RNA structures having a multi-branched loop, wherein the second assistive stem portion sequence is complementary to the first assistive stem portion sequence and hybridizes to the first assistive stem portion sequence to form a double-stranded assistive stem;
(4) adding a barcode region, which represents a complementary sequence to a DNA barcode sequence, to the assistive stem region; and
(5) synthesizing the RNA probe determined by the steps (1) to (4), wherein the RNA probe reflects a functional structural unit.

\* \* \* \* \*

UNITED STATES PATENT AND TRADEMARK OFFICE
CERTIFICATE OF CORRECTION

| | | |
|---|---|---|
| PATENT NO. | : 12,091,775 B2 | Page 1 of 1 |
| APPLICATION NO. | : 16/313329 | |
| DATED | : September 17, 2024 | |
| INVENTOR(S) | : Saito et al. | |

It is certified that error appears in the above-identified patent and that said Letters Patent is hereby corrected as shown below:

In the Specification

Column 12, Lines 16-17: Please insert a paragraph break between "solution." and "C." and make the following phrase a heading: C. Cy5 Fluorescence Labeling of RNA Probe Column 14, Line 17, Table 1: Please correct "BA038726_Muiti" to read --BA038726_Multi--

Signed and Sealed this
Tenth Day of December, 2024

Katherine Kelly Vidal
*Director of the United States Patent and Trademark Office*

SEQUENCE LISTING

```
<160> NUMBER OF SEQ ID NOS: 20

<210> SEQ ID NO 1
<211> LENGTH: 24
<212> TYPE: DNA
<213> ORGANISM: Artificial Sequence
<220> FEATURE:
<223> OTHER INFORMATION: CC + T7 promoter + G

<400> SEQUENCE: 1
ccgcgctaat acgactcact atag                                          24

<210> SEQ ID NO 2
<211> LENGTH: 18
<212> TYPE: DNA
<213> ORGANISM: Artificial Sequence
<220> FEATURE:
<223> OTHER INFORMATION: G + Stem forward sequence

<400> SEQUENCE: 2
ggtgtacgaa gtttcagc                                                 18

<210> SEQ ID NO 3
<211> LENGTH: 17
<212> TYPE: DNA
<213> ORGANISM: Artificial Sequence
<220> FEATURE:
<223> OTHER INFORMATION: Stem reverse sequence

<400> SEQUENCE: 3
gctgaagctt cgtgcac                                                  17

<210> SEQ ID NO 4
<211> LENGTH: 24
<212> TYPE: DNA
<213> ORGANISM: Artificial Sequence
<220> FEATURE:
<223> OTHER INFORMATION: Library forward Primer

<400> SEQUENCE: 4
ccgcgctaat acgactcact atag                                          24

<210> SEQ ID NO 5
```

```
<211> LENGTH: 25
<212> TYPE: DNA
<213> ORGANISM: Artificial Sequence
<220> FEATURE:
<223> OTHER INFORMATION: Library reverse Primer
<220> FEATURE:
<221> NAME/KEY: misc_feature
<222> LOCATION: (18)..(25)
<223> OTHER INFORMATION: n is a, c, g, or t

<400> SEQUENCE: 5
gtgcacgaag cttcagcnnn nnnnn                                          25

<210> SEQ ID NO 6
<211> LENGTH: 45
<212> TYPE: RNA
<213> ORGANISM: Artificial Sequence
<220> FEATURE:
<223> OTHER INFORMATION: pre-hsa-let-7d

<400> SEQUENCE: 6
gcauaguuuu agggcaggga uuuugcccac aaggagguaa cuaug                    45

<210> SEQ ID NO 7
<211> LENGTH: 51
<212> TYPE: RNA
<213> ORGANISM: Artificial Sequence
<220> FEATURE:
<223> OTHER INFORMATION: pre-hsa-mir-98

<400> SEQUENCE: 7
agcauuguug ugggguaggg auauuaggcc ccaauuagaa gauaacuaug c             51

<210> SEQ ID NO 8
<211> LENGTH: 39
<212> TYPE: RNA
<213> ORGANISM: Artificial Sequence
<220> FEATURE:
<223> OTHER INFORMATION: pre-hsa-let-7a-3

<400> SEQUENCE: 8
gcauaguuug gggcucugcc cugcuauggg auaacuaug                           39

<210> SEQ ID NO 9
<211> LENGTH: 40
<212> TYPE: RNA
<213> ORGANISM: Artificial Sequence
<220> FEATURE:
<223> OTHER INFORMATION: Rank2-GYG1

<400> SEQUENCE: 9
ccgugcgcgg ccacgugacg gccgcuauaa gagcgcacgg                          40

<210> SEQ ID NO 10
<211> LENGTH: 91
<212> TYPE: DNA
<213> ORGANISM: Artificial Sequence
<220> FEATURE:
<223> OTHER INFORMATION: Rank1_Pulldown_RNA_Probe_template

<400> SEQUENCE: 10
ggtgcacgag ggacccgcac cacctctcgc tcctccctcg tacacccag actcacagcc     60 gcgctagtat cctatagtga gtcgtattag c                                   91

<210> SEQ ID NO 11
<211> LENGTH: 85
```

```
<212> TYPE: DNA
<213> ORGANISM: Artificial Sequence
<220> FEATURE:
<223> OTHER INFORMATION: Rank8531_Pulldown_RNA_Probe_template

<400> SEQUENCE: 11
ggtgcacgag caggttagtc caaacacctg ctcgtacacc ccagactcac agccgcgcta      60
gtatcctata gtgagtcgta ttagc                                           85

<210> SEQ ID NO 12
<211> LENGTH: 114
<212> TYPE: DNA
<213> ORGANISM: Artificial Sequence
<220> FEATURE:
<223> OTHER INFORMATION: Rank5_Pulldown_RNA_Probe_template

<400> SEQUENCE: 12
ggtgcacgag cgggcccgca gcgtggcccc gcccctcccg cgcgccatcg ccccgcccgc      60
tcgtacaccc cagactcaca gccgcgctag tatcctatag tgagtcgtat tagc           114

<210> SEQ ID NO 13
<211> LENGTH: 140
<212> TYPE: DNA
<213> ORGANISM: Artificial Sequence
<220> FEATURE:
<223> OTHER INFORMATION: Rank10_Pulldown_RNA_Probe_template

<400> SEQUENCE: 13
ggtgcacgag ggcctttctg tatcattatg gtagctggat ttgttacttg gctcattgct     60
tcagccaaaa ctcttgcttt atggcctcgt acacccnaga ctcacagccg cgctagtatc    120
ctatagtgag tcgtattagc                                                140

<210> SEQ ID NO 14
<211> LENGTH: 149
<212> TYPE: DNA
<213> ORGANISM: Artificial Sequence
<220> FEATURE:
<223> OTHER INFORMATION: Rank19(PC,-4stem)_Pulldown_RNA_Probe_template

<400> SEQUENCE: 14
ggtgcacgag ggccaggatt aactgcgaat cgttctagct ccctgcttgc ccatactata     60
tgttttagtt tatattgttt ctttccccct ggcctcgta cacccagac tcacagccgc      120 gctagtatcc tatagtgagt cgtattagc                                      149

<210> SEQ ID NO 15
<211> LENGTH: 72
<212> TYPE: RNA
<213> ORGANISM: Artificial Sequence
<220> FEATURE:
<223> OTHER INFORMATION: Rank1_Pulldown_RNA_Probe

<400> SEQUENCE: 15
ggauacuagc gcggcuguga gucuggggug uacgagggag gagcgagagg uggugcgggu      60
cccucgugca cc                                                         72

<210> SEQ ID NO 16
<211> LENGTH: 66
<212> TYPE: RNA
<213> ORGANISM: Artificial Sequence
<220> FEATURE:
<223> OTHER INFORMATION: Rank8531_Pulldown_RNA_Probe
```

```
<400> SEQUENCE: 16
ggauacuagc gcggcuguga gucuggggug uacgagcagg uguuuggacu aaccugcucg      60
ugcacc                                                                 66

<210> SEQ ID NO 17
<211> LENGTH: 95
<212> TYPE: RNA
<213> ORGANISM: Artificial Sequence
<220> FEATURE:
<223> OTHER INFORMATION: Rank5_Pulldown_RNA_Probe

<400> SEQUENCE: 17
ggauacuagc gcggcuguga gucuggggug uacgagcggg cggggcgaug gcgcgcggga      60
ggggcggggc cacgcugcgg gcccgcucgu gcacc                                 95

<210> SEQ ID NO 18
<211> LENGTH: 121
<212> TYPE: RNA
<213> ORGANISM: Artificial Sequence
<220> FEATURE:
<223> OTHER INFORMATION: Rank10_Pulldown_RNA_Probe

<400> SEQUENCE: 18
ggauacuagc gcggcuguga gucuggggug uacgaggcca uaaagcaaga guuuggcug       60 aagcaaugag ccaaguaaca aauccagcua ccauaaugau acagaaaggc ccucgugcac     120
c                                                                    121

<210> SEQ ID NO 19
<211> LENGTH: 130
<212> TYPE: RNA
<213> ORGANISM: Artificial Sequence
<220> FEATURE:
<223> OTHER INFORMATION: Rank19(PC,-4stem)_Pulldown_RNA_Probe

<400> SEQUENCE: 19
ggauacuagc gcggcuguga gucuggggug uacgagggcc aggggggaaag aaacaauaua     60 aacuaaaaca uauaguaugg gcaagcaggg agcuagaacg auucgcaguu aauccuggcc    120
cucgugcacc                                                           130

<210> SEQ ID NO 20
<211> LENGTH: 29
<212> TYPE: DNA
<213> ORGANISM: Artificial Sequence
<220> FEATURE:
<223> OTHER INFORMATION: 3'-biotinylated DNA Probe Barcode 25mer + C +
    3spacer

<400> SEQUENCE: 20
ccagactcac agccgcgcta gtatccaag                                        29
```